United States Patent
Ye

(10) Patent No.: US 10,495,715 B2
(45) Date of Patent: Dec. 3, 2019

(54) SYSTEMS AND METHODS FOR COMPENSATING GRADIENT PULSE OF MRI

(71) Applicant: UIH AMERICA, INC., Houston, TX (US)

(72) Inventor: Yongquan Ye, Houston, TX (US)

(73) Assignee: UIH AMERICA, INC., Houston, TX (US)

( * ) Notice: Subject to any disclaimer, the term of this patent is extended or adjusted under 35 U.S.C. 154(b) by 267 days.

(21) Appl. No.: 15/606,149

(22) Filed: May 26, 2017

(65) Prior Publication Data

US 2018/0340998 A1    Nov. 29, 2018

(51) Int. Cl.
*G01R 33/565*    (2006.01)
*A61B 5/055*    (2006.01)

(52) U.S. Cl.
CPC ........ *G01R 33/56509* (2013.01); *A61B 5/055* (2013.01); *G01R 33/56572* (2013.01)

(58) Field of Classification Search
CPC ........ G01R 33/56509; G01R 33/56572; A61B 5/055
See application file for complete search history.

(56) References Cited

PUBLICATIONS

Robert W. Brown, et al, Motion Artifacts and flow compensation (Chapter 23), pp. 669-700, Magnetic Resonance Imaging: Physical Principles and Sequence Design, 2nd Edition, 2014 (Year: 2014).*
Wu, Dongmei, et al., A Fully Flow-Compensated Multiecho Susceptibility-Weighted Imaging Sequence: The Effects of Acceleration and Background Field on Flow Compensation: Magnetic Res. in Med. 76:478-489(2016).
Ye, Yongquan, et al., Noncontrast-Enhanced Magnetic Resonance Angiography and Venography Imaging With Enhanced Angiography: Journal of Magnetic Resonance Imaging 38: 1539-1548(2013).

* cited by examiner

*Primary Examiner* — Daniel R Miller
(74) *Attorney, Agent, or Firm* — Metis IP LLC

(57) ABSTRACT

A method for determining a flow sensitive gradient block includes determine a gradient parameter for one or more echoes in an imaging sequence according to a scanning protocol. The method also includes determining one or more time origins for gradient moment calculation based on the gradient parameter and obtaining one or more target zeroth-order gradient moments and one or more target first-order gradient moments corresponding to the one or more time origins. The method further includes determining one or more parameters of the one or more flow sensitive gradient blocks with respect to the one or more target zeroth-order gradient moments and the one or more target first-order gradient moment and updating the gradient parameter according to the one or more parameters of the one or more flow sensitive gradient blocks.

20 Claims, 13 Drawing Sheets

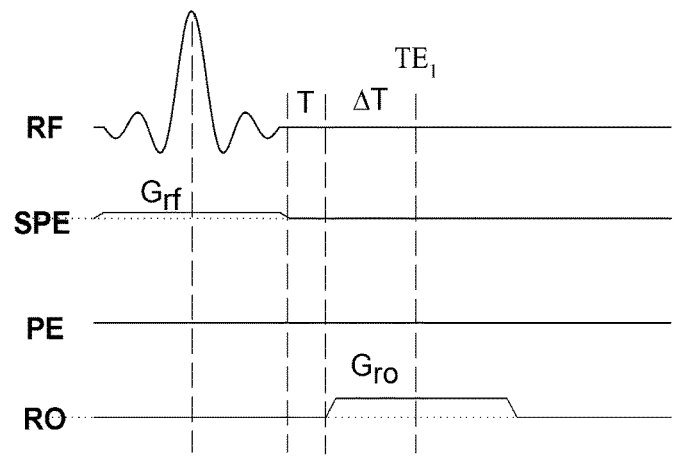
FIG. 10-A
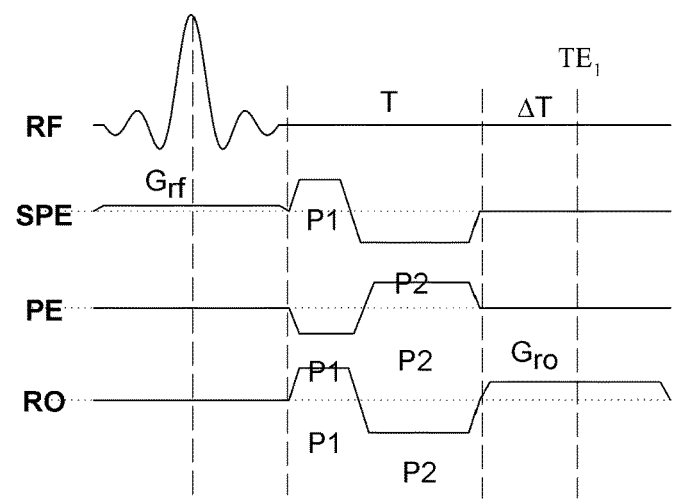
FIG. 10-B
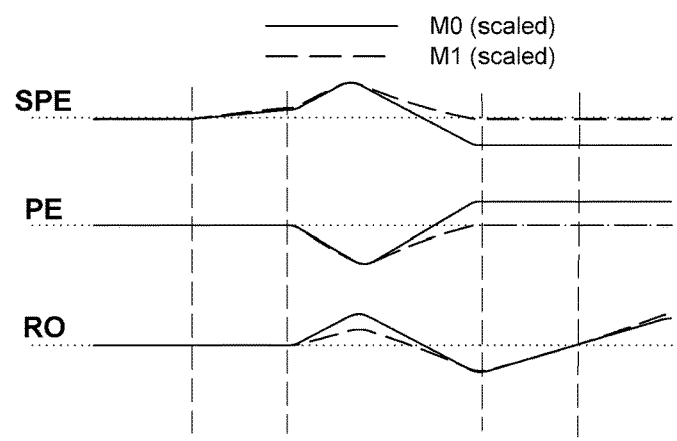
FIG. 10-C

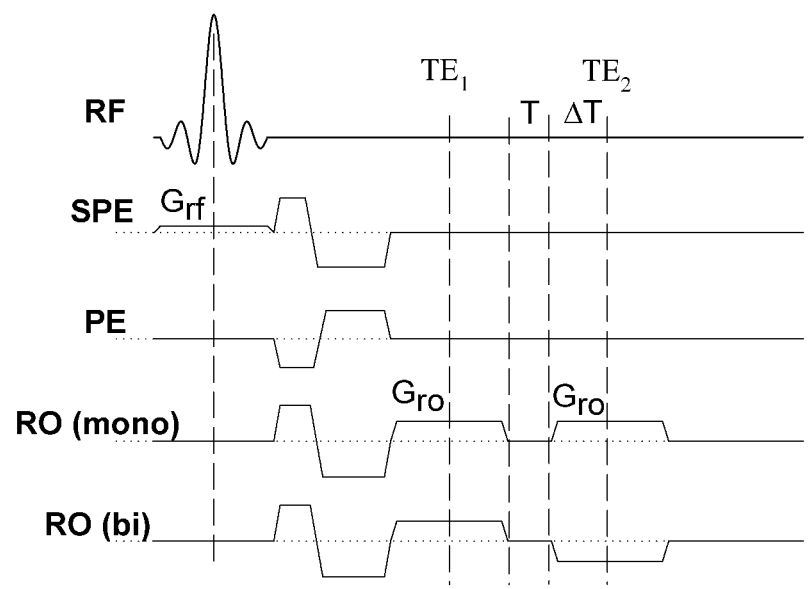
FIG. 11-A

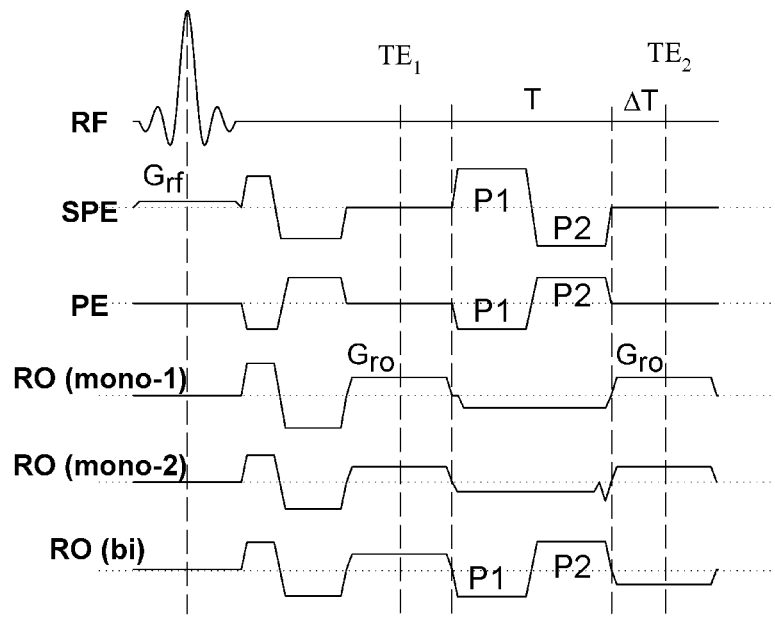
FIG. 11-B
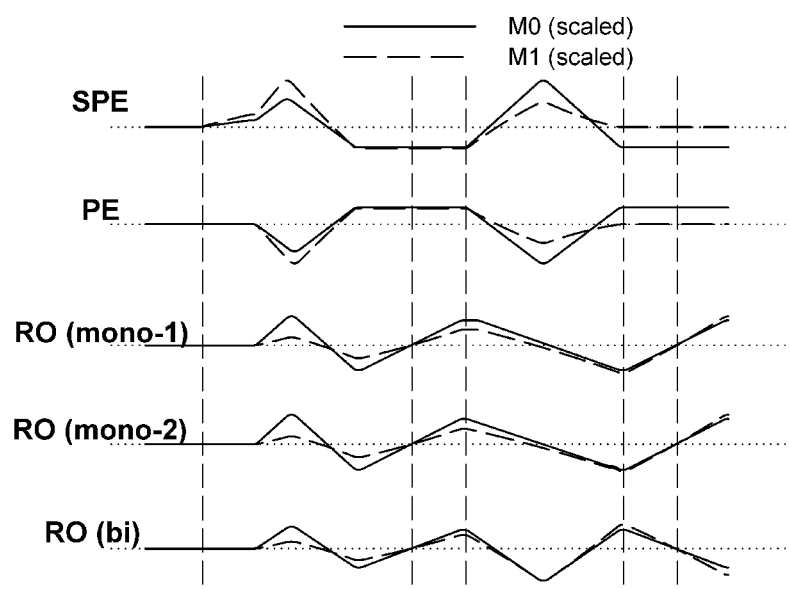
FIG. 11-C

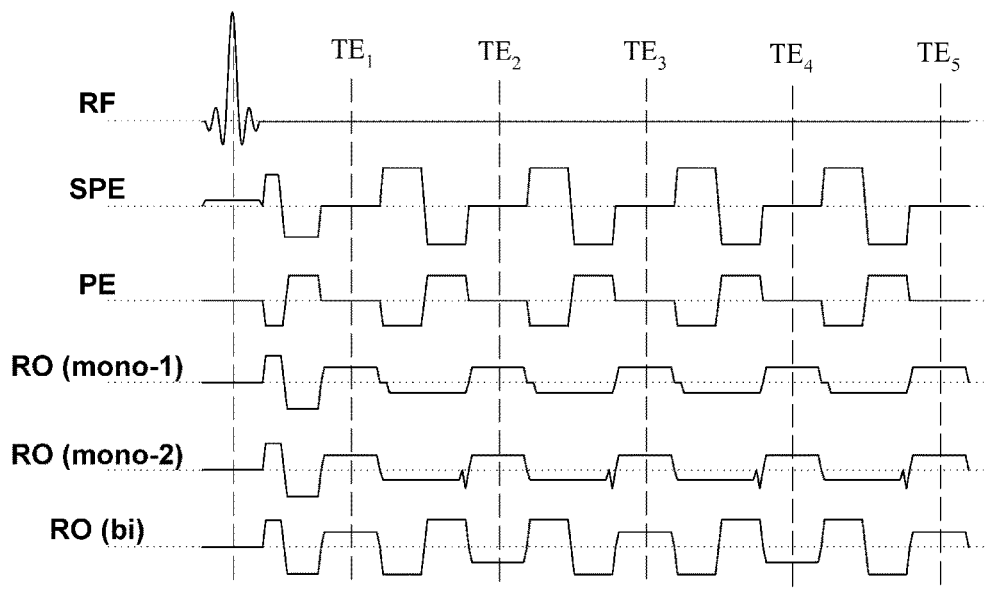
FIG. 12-A
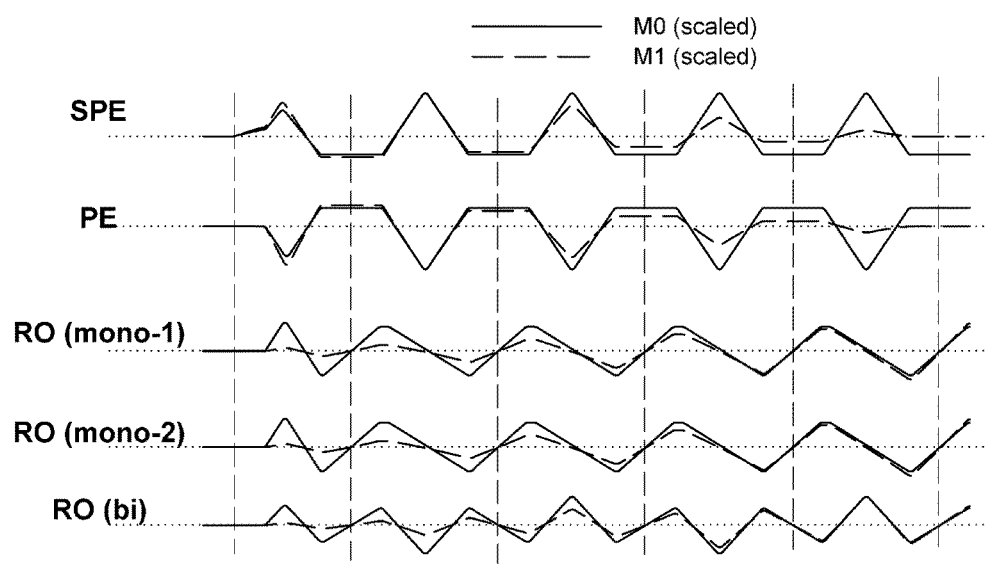
FIG. 12-B

SYSTEMS AND METHODS FOR COMPENSATING GRADIENT PULSE OF MRI

TECHNICAL FIELD

The present disclosure generally relates to a magnetic resonance imaging (MRI) system, and more particularly, relates to systems and methods for compensating gradient pulse of MRI.

BACKGROUND

Magnetic resonance imaging (MRI) is a technology that makes use of one or more gradient pluses to encode spatial information to MR signals for reconstructing images. The MRI technology has been widely used in medical diagnosis. During a scanning process, fluid flow (e.g., blood or cerebrospinal fluid flow) may affect the spatial encoding to MR signals. It may be desirable to provide systems and methods for determining a flow sensitive gradient block accurately.

SUMMARY

According to an aspect of the present disclosure, a system may include at least one non-transitory computer-readable storage medium including a set of instructions, and at least one processor in communication with the at least one non-transitory computer-readable storage medium, wherein when executing the instructions, the at least one processor is configured to cause the system to determine an imaging gradient parameter according to a scanning protocol, determine a time origin for gradient moment calculation and a target condition for a flow sensitive gradient block associated with the time origin determine a parameter of a flow sensitive gradient block according to the target condition, and adjust the imaging gradient parameter according to the parameter of the flow sensitive gradient block. In some embodiments, the flow sensitive gradient block may include at least one flow sensitive gradient. In some embodiments, the parameter of the flow sensitive gradient block may include at least one duration and at least one amplitude value of the at least one flow sensitive gradient.

In some embodiments, the flow sensitive gradient block may include a first flow sensitive gradient and a second flow sensitive gradient.

In some embodiments, the target condition may include a target zeroth-order gradient moment and a target first-order gradient moment associated with the flow sensitive gradient block.

In some embodiments, the at least one processor may be configured to cause the system to initialize a first duration and a time difference associated with the flow sensitive gradient block, the first duration being a time length of the flow sensitive gradient block and the time difference being a distance between the time origin and a time point of the flow sensitive gradient block.

In some embodiments, the at least one processor may be configured to cause the system to determine a first amplitude value of the first flow sensitive gradient and a second amplitude value of the second flow sensitive gradient, determine the first amplitude value and the second amplitude value are equal to or less than a threshold, and in response to the determination that the first amplitude value and the second amplitude value are equal to or less than the threshold, determine the first duration as the duration of the flow sensitive gradient block.

In some embodiments, the at least one processor may be configured to cause the system to determine a first amplitude value of the first flow sensitive gradient and a second amplitude value of the second flow sensitive gradient, determine the first amplitude value and the second amplitude value are larger than a threshold, and in response to the determination that the first amplitude value and the second amplitude value are larger than the threshold, determine a second duration by adjusting the first duration as the duration of the flow sensitive gradient block.

In some embodiments, the parameter of the flow sensitive gradient block may include a component on a slice selecting axis, a component on a phase encoding axis, and a component on a readout coordinate axis.

In some embodiments, the at least one processor may be configured to cause the system to determine an optimal duration associated with the slice selecting axis, an optimal duration associated with the phase encoding axis, and an optimal duration associated with the readout coordinate axis and determine a shared duration for the phase encoding axis, the phase encoding axis, and the readout coordinate axis based on the optimal durations.

In some embodiments, the at least one processor may be configured to cause the system to determine modify the parameter of the flow sensitive gradient block based on the first duration, and insert the modified flow sensitive gradient block into the imaging gradient parameter.

In some embodiments, the scanning protocol may be associated to a pulse sequence of one or more echoes.

In some embodiments, the flow sensitive gradient block may be used to perform at least one function of flow encoding, flow compensation, or flow dephasing.

According to an aspect of the present disclosure, a method, implemented on a computing device having at least one processor, at least one computer-readable storage medium, and a communication port connected to an imaging device for determining, by the at least one processor, a gradient parameter for a first echo in an imaging sequence according to a scanning protocol. The method may include determining, by the at least one processor, a first time origin for gradient moment calculation based on the gradient parameter. The method also include obtaining, by the at least one processor, at least a target zeroth-order gradient moment and a target first-order gradient moment corresponding to the first time origin. The method may further include determining, by the at least one processor, a first parameter of a first flow sensitive gradient block with respect to the target zeroth-order gradient moment and the target first-order gradient moment. The method may also include updating, by the at least one processor, the gradient parameter according to the first parameter of the first flow sensitive gradient block.

In some embodiments, the imaging sequence may be a single-echo sequence, and the gradient parameter may correspond to a single-pulse field gradient or a double-pulse field gradient.

In some embodiments, the first flow sensitive gradient block may include a first sensitive gradient and a second sensitive gradient. The method may further include initializing a first duration and a time difference associated with the first flow sensitive gradient block, the first duration being a time length of the first flow sensitive gradient block, the time difference being a distance between the first time origin and a time point of the first flow sensitive gradient block.

In some embodiments, the method may further include determining a first amplitude value of the first flow sensitive gradient and a second amplitude value of the second flow sensitive gradient; determining the first amplitude value and the second amplitude value equal to or less than a threshold; and in response to the determination that the first amplitude value and the second amplitude value are equal to or less than the threshold, determining the first duration as the duration of the first flow sensitive gradient block.

In some embodiments, the method may further include determining a first amplitude value of the first flow sensitive gradient and a second amplitude value of the second flow sensitive gradient; determining the first amplitude value and the second amplitude value are larger than a threshold; and in response to the determination that the first amplitude value and the second amplitude value are larger than the threshold, determining a second duration by adjusting the first duration as the duration of the first flow sensitive gradient block.

In some embodiments, the method may further include determining an optimal duration associated with the slice selecting axis, an optimal duration associated with the phase encoding axis, and an optimal duration associated with the readout coordinate axis; and determining a shared duration for the phase encoding axis, the phase encoding axis, and the readout coordinate axis based on the optimal durations.

In some embodiments, the imaging sequence may further comprise a second echo, and the method further include determining an imaging gradient parameter for the second echo; determining a second time origin for the gradient moment calculation based on the gradient parameter for the second echo; obtaining at least a target zeroth-order gradient moment and a target first-order gradient moment corresponding to the second time origin; determining a second parameter of a second flow sensitive gradient block with respect to the target zeroth-order gradient moment and the target first-order gradient moment; and updating the gradient parameter according to the second parameter of the second flow sensitive gradient block.

In some embodiments, the target zeroth-order gradient moment and the target first-order gradient moment corresponding to the first time origin are independent of the target zeroth-order gradient moment and the target first-order gradient moment corresponding to the second time origin.

In some embodiments, the method further include exciting nuclear spine in a volume of a subject based on the updated gradient parameter, the volume may comprise a flow; acquiring magnetic resonance signals for the volume; and generating a magnetic resonance image of the volume with the flow based on the magnetic resonance signals.

According to another aspect of the present disclosure, a non-transitory computer readable medium embodying a computer program product may be provided. The computer program product may include the instructions that are configured to cause a computing device to determine an imaging gradient parameter for one or more echoes in the imaging sequence. The computer program product may also include the instructions that are configured to cause the computing device to determine one or more time origins for gradient moment calculation based on the gradient parameter and obtain one or more target zeroth-order gradient moments and one or more target first-order gradient moments corresponding to the one or more time origins. The computer program product may further include the instructions that are configured to cause the computing device to determine one or more parameters of the one or more flow sensitive gradient blocks with respect to the one or more target zeroth-order gradient moments and the one or more target first-order gradient moment and update the gradient parameter according to the one or more parameters of the one or more flow sensitive gradient blocks.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 10-A illustrates exemplary diagrams of a single echo pulse sequence according to some embodiments of the present disclosure;

FIG. 10-B illustrates exemplary diagrams of a single echo pulse sequence according to some embodiments of the present disclosure;

FIG. 10-C illustrates exemplary diagrams of curves respecting to zeroth-order gradient moment M0 and first-order gradient moment M1 varied with time according to some embodiments of the present disclosure;

FIG. 11-A illustrates exemplary diagrams of a double echo pulse sequence according to some embodiments of the present disclosure;

FIG. 11-B illustrates exemplary diagrams of a double echo sequence according to some embodiments of the present disclosure;

FIG. 11-C illustrates exemplary diagrams of curves respecting to zeroth-order gradient moment M0 and first-order gradient moment M1 varied with time according to some embodiments of the present disclosure;

FIG. 12-A illustrates exemplary diagrams of a multi-echoes sequence according to some embodiments of the present disclosure; and FIG. 12-B illustrates exemplary diagrams of curves respecting to zeroth-order gradient moment M0 and first-order gradient moment M1 varied with time according to some embodiments of the present disclosure.

DETAILED DESCRIPTION

The following description is presented to enable any person skilled in the art to make and use the present disclosure, and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but is to be accorded the widest scope consistent with the claims.

The terminology used herein is for the purpose of describing particular exemplary embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," and/or "module" used herein are one method to distinguish different components, elements, parts, section or assembly of different level in ascending order. However, the terms may be displaced by other expression if they achieve the same purpose.

Figure 3:
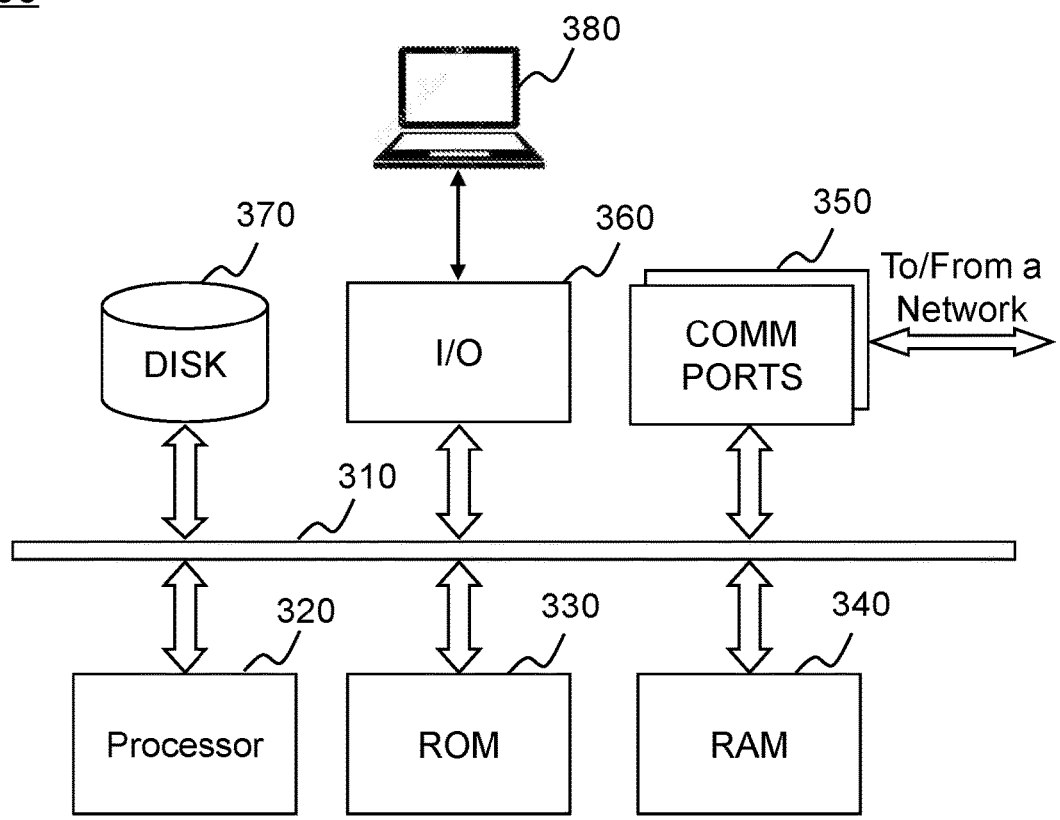
FIG. 3 is a schematic diagram illustrating exemplary hardware and/or software components of an exemplary computing device according to some embodiments of the present disclosure.

Generally, the word "module" or "unit" as used herein, refers to logic embodied in hardware or firmware, or to a collection of software instructions. A module or a unit described herein may be implemented as software and/or hardware and may be stored in any type of non-transitory computer-readable medium or other storage device. In some embodiments, a software module/unit may be compiled and linked into an executable program. It will be appreciated that software modules can be callable from other modules/units or from themselves, and/or may be invoked in response to detected events or interrupts. Software modules/units configured for execution on computing devices (e.g., processor 320 as illustrated in FIG. 3) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in a firmware, such as an EPROM. It will be further appreciated that hardware modules/units may be included in connected logic components, such as gates and flip-flops, and/or can be included of programmable units, such as programmable gate arrays or processors. The modules/units or computing device functionality described herein may be implemented as software modules/units, but may be represented in hardware or firmware. In general, the modules/units described herein refer to logical modules/units that may be combined with other modules/units or divided into sub-modules/sub-units despite their physical organization or storage. The description may be applicable to a system, an engine, or a portion thereof.

It will be understood that when a unit, engine or module is referred to as being "on," "connected to," or "coupled to," another unit, engine, or module, it may be directly on, connected or coupled to, or communicate with the other unit, engine, or module, or an intervening unit, engine, or module may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of the present disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood, the operations of the flowcharts may be implemented not in order. Conversely, the operations may be implemented in inverted order, or simultaneously. Moreover, one or more other operations may be added to the flowcharts. One or more operations may be removed from the flowcharts.

Figure 1:
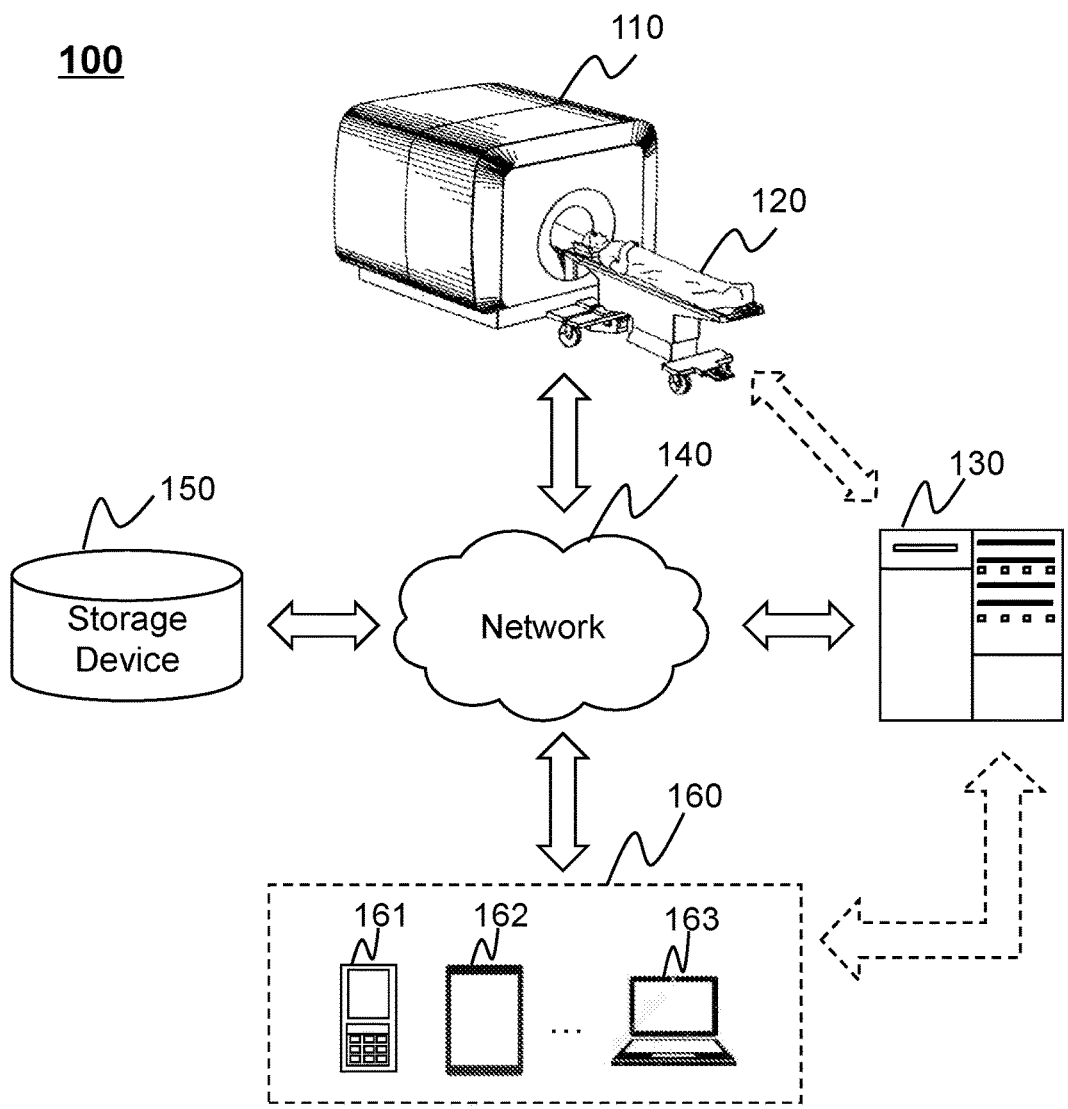
FIG. 1 is a block diagram illustrating an exemplary imaging system according to some embodiments of the present disclosure.

FIG. 1 is a block schematic diagram illustrating an exemplary imaging system according to some embodiments of the present disclosure. The imaging system 100 may be a magnetic resonance imaging (MRI) system, a positron emission tomography-magnetic resonance imaging (PET-MRI) system, a digital subtraction angiography-magnetic resonance, or the like, or any combination thereof. For example, the mobile device 161 may include a mobile phone, a personal digital assistance (PDA), a gaming device, a navigation device, a point of sale (POS) device, a laptop, a tablet computer, a desktop, or the like, or any combination thereof. In some embodiments, the terminal device 160 may include an input device, an output device, etc. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to the processing engine 130 via, for example, a bus, for further processing. Other types of the input device may include a cursor control device, such as a mouse, a trackball, or cursor direction keys, etc. The output device may include a display, a speaker, a printer, or the like, or any combination thereof. In some embodiments, the terminal device 160 may be part of the processing engine 130.

This description is intended to be illustrative, and not to limit the scope of the present disclosure. Many alternatives, modifications, and variations will be apparent to those skilled in the art. The features, structures, methods, and characteristics of the exemplary embodiments described herein may be combined in various ways to obtain additional and/or alternative exemplary embodiments. For example, the storage device 150 may be a data storage including cloud computing platforms, such as, public cloud, private cloud, community, hybrid clouds, etc. In some embodiments, the processing engine 130 may be integrated into the MR scanner 110. However, those variations and modifications do not depart the scope of the present disclosure.

Figure 2:
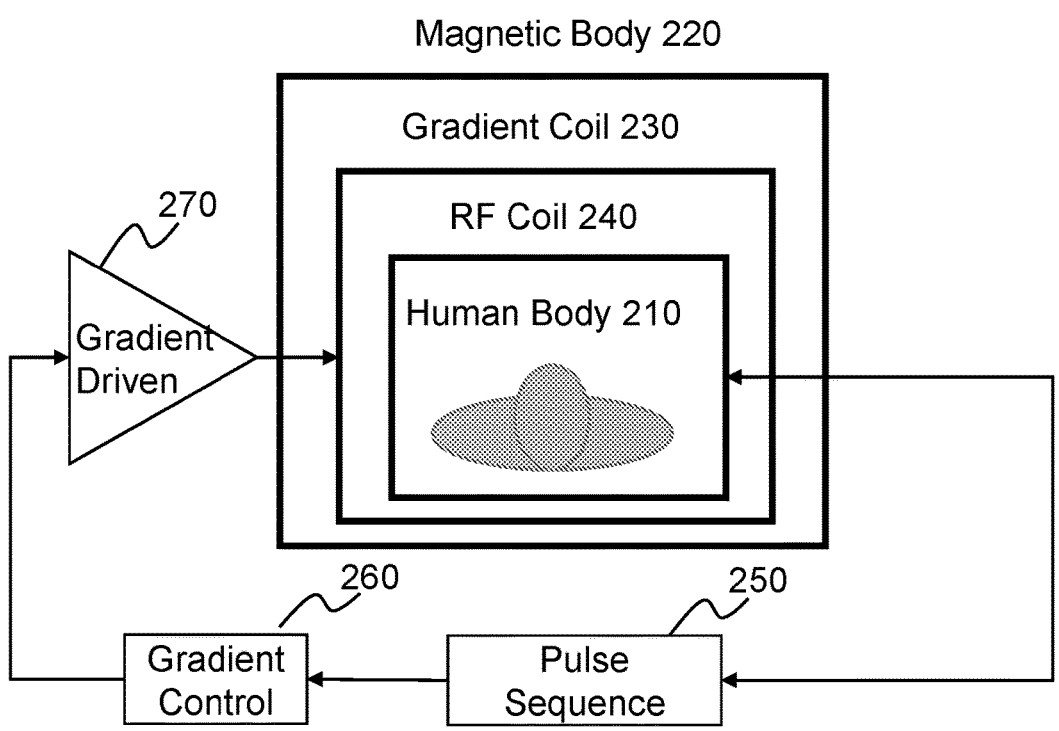
FIG. 2 is a block diagram illustrating an exemplary MR scanner according to some embodiments of the present disclosure.

FIG. 2 is a block diagram illustrating an exemplary MR scanner according to some embodiments of the present disclosure. As shown in the FIG. 2, the MR scanner 110 may include a magnetic body 220, a gradient coil 230, an RF coil 240, a pulse sequence 250, a gradient control 260, and a gradient driven 270.

The magnetic body 220 may generate a static magnetic field BO during an MRI process. The magnetic body 220 may be of various types including, for example, a permanent magnet, a superconducting electromagnet, a resistive electromagnet, etc.

The gradient coil 230 may generate magnetic field gradients to the main magnetic field BO in the X, Y, and/or Z directions (or axes). In some embodiments, the gradient coil 230 may include an X-direction coil (or axis), a Y-direction coil (or axis), a Z-direction coil (or axis), etc. For example, the Z-direction coil may be designed based on circular (Maxwell) coil, while the X-direction coil and the Y-direction coil may be designed on the basis of the saddle (Golay) coil configuration. As used herein, the X direction may be also referred to as the readout (RO) direction (or a frequency encoding direction), the Y direction may be also referred to the phase encoding (PE) direction, the Z direction may be also referred to the slice selecting encoding (SPE) direction. In the present disclosure, the readout direction and the frequency encoding direction may be used interchangeably.

The gradient magnetic fields may include a slice selecting encoding (SPE) gradient field corresponding to Z-direction, a phase encoding (PE) gradient field corresponding to Y-direction, a readout (RO) gradient field corresponding to X-direction, etc. The gradient magnetic fields on different directions may be used to encode the spatial information of MR signals. In some embodiments, the gradient magnetic fields may be also used to perform at least one function of flow encoding, flow compensation, flow dephasing, or the like, or any combination thereof.

The RF coil 240 may emit RF pulse signals to and/or receive MR signals from a human body 210 being examined. In some embodiments, the RF coil 240 may include an RF transmitting coil and an RF receiving coil. The RF transmitting coil may emit RF pulse signals that may excite the nucleus in the human body 210 to resonate at the Larmor frequency. The RF receiving coil may receive MR signals emitted from the human body 210. In some embodiments, the RF transmitting coil and RF receiving coil may be integrated into one single coil, for example, a transmitting/receiving coil. The RF coil 240 may be of various types including, for example, a QD orthogonal coil, a phase-array coil, a specific element spectrum coil, etc. In some embodiments, the RF coil 240 may be different according to different parts of a body being examined, for example, a head coil, a knee joint coil, a cervical vertebra coil, a thoracic vertebra coil, a temporomandibular joint (TMJ) coil, etc. In some embodiments, according to function and size, the RF coil 240 may be classified as a volume coil and a local coil. For example, the volume coil may include a birdcage coil, a transverse electromagnetic coil, a surface coil, a saddle coil, etc. As another example, the local coil may include a solenoid coil, a saddle coil, a flexible coil, etc.

The pulse sequence 250 may have several portions including, for example, an RF pulse, an MR signal, a phase encoding (PE) gradient, a readout (RO) gradient, a slice selecting encoding (SPE) gradient, etc. In some embodiments, the pulse sequence 250 may include a flow sensitive gradient block/module (hereinafter referred to as "flow sensitive gradient block"). The flow sensitive gradient block may be a flow sensitive gradient added to at least one directions corresponding to the phase encoding (PE) gradient, the readout (RO) gradient, or the slice selecting encoding (SPE) gradient.

The pulse sequence 250 may be defined by imaging gradient parameters and arrangement in time sequence corresponding to the imaging gradient parameters. In some embodiments, the imaging gradient parameters may include parameters related to an RF pulse emitted by the RF coil 240, the parameters related to gradient fields generated by the gradients coil 230, and the time for collecting MR signals. The different portions of the pulse sequence 250, such as (the RF pulse, the imaging gradient, etc.) may refer to different imaging gradient parameters. For example, the RF pulse block may refer to parameters related to an RF pulse, such as a bandwidth (also referred to as a frequency range), an amplitude or strength, a time for applying the RF pulse, a duration for applying the RF pulse, etc. The parameters related to the imaging gradient may include an amplitude value of the gradient pulses, a duration of an imaging gradient, a starting time for applying an imaging gradient, an ending time for applying an imaging gradient, etc. The parameters related to the MR signals may include MR signals types, a number of echoes, centers of the echoes, time of echoes, etc.

In some embodiments, the pulse sequence 250 may be a free-induction decay (FID) sequence, a spin echo (SE) sequence, a gradient echo (GRE) sequence, a fast imaging with stead-state precession (FISP) sequence, or the like, or any combination thereof.

In some embodiments, the pulse sequence 250 may be connected to and/or communicate with the processing engine 130. For example, before an MRI scanning process, at least one portion of the pulse sequence 250 (e.g., the RF pulse, the imaging gradient) may be designed and/or determined by the processing engine 130 according to clinical demands or a scanning protocol. In the MRI scanning process, the RF coil 240 may emit RF pulses with specific parameters related to the RF pulse of the pulse sequence 250, and receive MR signals. The MR signals may compose one portion of the pulse sequence 250. The gradient control 260 may control the gradient driven 270 to drive the gradient coil 230 by gradient pulses with specific parameters related to the imaging gradient of the pulse sequence 250. The gradient fields generated by the gradient coil 230 may encode the MR signals. The encoded MR signals may be transmitted to the processing engine 130 for determining an MR image.

This description is intended to be illustrative, and not to limit the scope of the present disclosure. Many alternatives, modifications, and variations will be apparent to those skilled in the art. The features, structures, methods, and characteristics of the exemplary embodiments described herein may be combined in various ways to obtain additional and/or alternative exemplary embodiments. For example, the MR scanner 110 may include a sending channel and/or a receiving channel for sending and receiving information (e.g., RF pulse, imaging gradient, etc.). However, those variations and modifications do not depart the scope of the present disclosure.

FIG. 3 is a schematic diagram illustrating exemplary hardware and/or software components of an exemplary computing device on which the processing engine 130 may be implemented according to some embodiments of the present disclosure. The processing engine 130 may be implemented on the computing device via its hardware, software program, firmware, or any combination thereof. Although only one such computing device is shown, for convenience, the functions of the processing engine 130 described in the present disclosure may be implemented in a distributed fashion on a number of similar platforms, to distribute the processing load. The processing engine 130 may include, among other things, an internal communication bus 310, a processor 320, a program storage and data storage of different forms (e.g., a disk 370, a read only memory (ROM) 330, or a random access memory (RAM) 340), for various data files to be processed and/or communicated by the computer, as well as possibly program instructions to be executed by processor 320. Aspects of the methods of the image processing and/or other processes, as outlined herein, may be embodied in programming. Program aspects of the technology may be thought of as "products" or "articles of manufacture" typically in the form of executable code and/or associated data that is carried on or embodied in a type of machine readable medium. Tangible non-transitory "storage" type media may include any or all of the memory or other storage for the computers, processors, or the like, or associated modules thereof, such as various semiconductor memories, tape drives, disk drives and the like, which may provide storage at any time for the software programming.

All or portions of the software may at times be communicated through a network such as the Internet or various other telecommunication networks. Such communications, for example, may enable loading of the software from one computer or processor into another, for example, from a management server or host computer of a mammography system into the hardware platform(s) of a computing environment or other system implementing a computing environment or similar functionalities in connection with the image processing. Thus, another type of media that may bear the software elements includes optical, electrical, and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to tangible "storage" media, terms such as computer or machine "readable medium" refer to any medium that participates in providing instructions to a processor for execution.

A computer-readable medium may take many forms including, for example, a tangible storage medium, a carrier wave medium, or physical transmission medium. Non-volatile storage media include, for example, optical or magnetic disks, such as any of the storage devices in any computer(s) or the like, which may be used to implement the system or any of its components as shown in the drawings. Volatile storage media may include dynamic memory, such as a main memory of such a computer platform. Tangible transmission media may include coaxial cables; copper wire and fiber optics, including the wires that form a bus within a computer system. Carrier-wave transmission media may take the form of electric or electromagnetic signal, or acoustic or light waves such as those generated during radio frequency (RF) and infrared (IR) data communications. Common forms of computer-readable media therefore may include for example: a floppy disk, a flexible disk, a hard disk, a magnetic tape, any other magnetic medium, a CD-ROM, a DVD or DVD-ROM, any other optical medium, punch cards paper tape, any other physical storage medium with patterns of holes, a RAM, a PROM or an EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a physical processor for execution.

The processor 320 may execute program instructions stored in a storage device (e.g., disk 370, ROM 330, RAM 340) to perform one or more functions of the processing engine 130 described in the present disclosure. The processor 320 may include a central processing unit (CPU), an application-specific integrated circuit (ASIC), an application-specific instruction-set processor (ASIP), a graphics processing unit (GPU), a physics processing unit (PPU), a digital signal processor (DSP), a field programmable gate array (FPGA), a programmable logic device (PLD), a microcontroller unit, an advanced RISC machines processor (ARM), or the like, or a combination thereof.

The I/O 360 may input and/or output signals, data, information, etc. In some embodiments, the I/O 360 may enable a user interaction with the processing engine 130. In some embodiments, the I/O 360 may include an input device and an output device. Examples of the input device may include a keyboard, a mouse, a touch screen, a microphone, or the like, or any combination thereof. Examples of the output device may include a display device, a loudspeaker, a printer, a projector, or the like, or any combination thereof. Examples of the display device may include a liquid crystal display (LCD), a light-emitting diode (LED)-based display, a flat panel display, a curved screen, a television device, a cathode ray tube (CRT), a touch screen, or the like, or any combination thereof.

The communication port 350 may be connected to a network (e.g., the network 140) to facilitate data communications. The communication port 350 may establish connections between the MR scanner 110, the examining table 120, the processing engine 130, the terminal device 160, and/or the storage device 150. The connection may be a wired connection, a wireless connection, any other communication connection that can enable data transmission and/or reception, or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or any combination thereof. In some embodiments, the communication port 350 may be and/or include a standardized communication port, such as RS232, RS485, etc. In some embodiments, the communication port 350 may be a specially designed communication port. For example, the communication port 350 may be designed in accordance with the digital imaging and communications in medicine (DICOM) protocol.

Those skilled in the art will recognize that the present teachings are amenable to a variety of modifications and/or enhancements. For example, although the implementation of various components described herein may be embodied in a hardware device, it may also be implemented as a software only solution, for example, an installation on an existing server. In addition, the processing engine 130 as disclosed herein may be implemented as a firmware, firmware/software combination, firmware/hardware combination, or a hardware/firmware/software combination.

Figure 4:
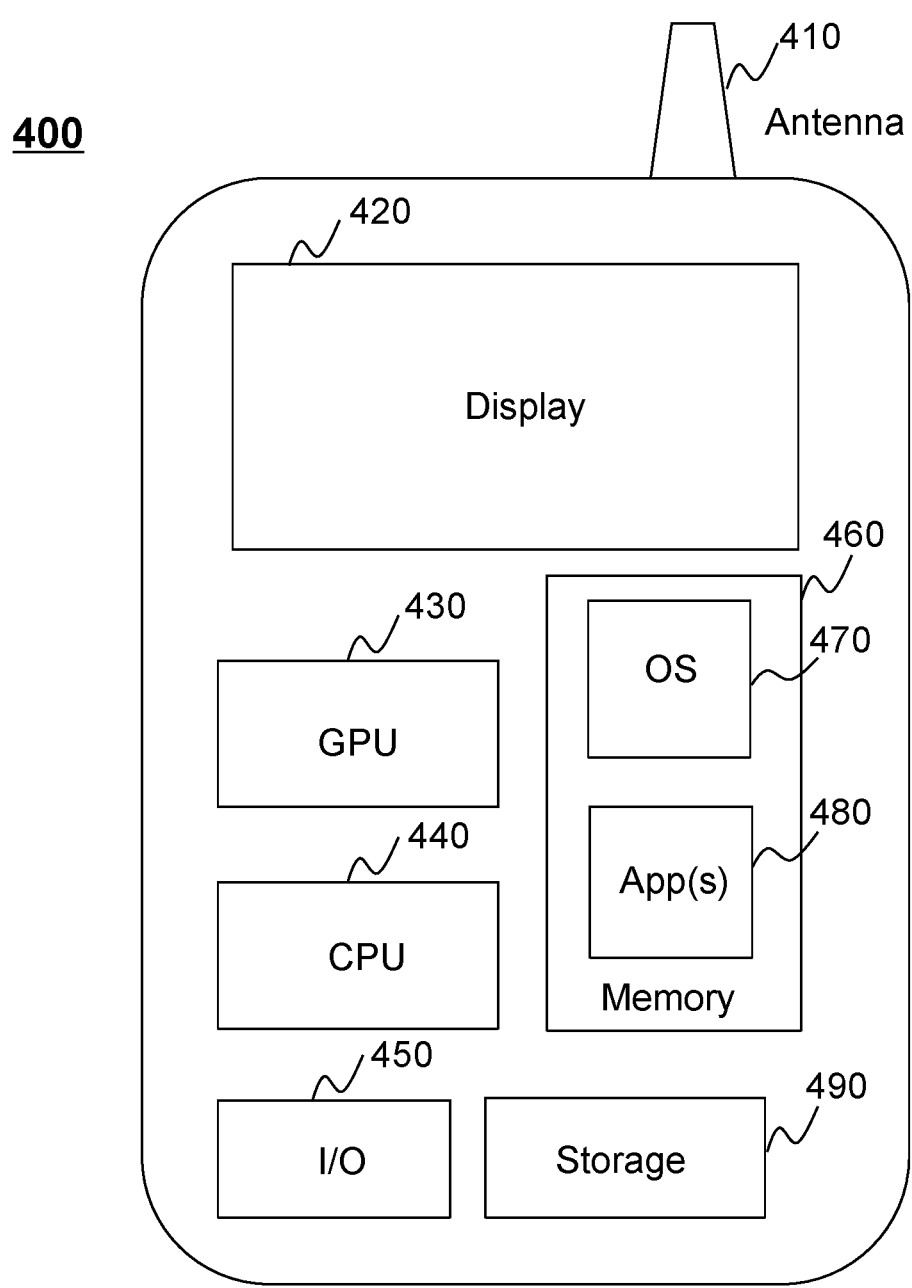
FIG. 4 is a schematic diagram illustrating exemplary hardware and/or software components of an exemplary mobile device on which a user terminal may be implemented according to some embodiments of the present disclosure.

FIG. 4 is a schematic diagram illustrating exemplary hardware and/or software components of an exemplary mobile device on which the terminal device 160 may be implemented according to some embodiments of the present disclosure. As illustrated in FIG. 4, the mobile device 400 may include a communication platform 410, a display 420, a graphic processing unit (GPU) 430, a central processing unit (CPU) 440, an I/O 450, a memory 460, and a storage 490. In some embodiments, any other suitable component, including but not limited to a system bus or a controller (not shown), may also be included in the mobile device 400. In some embodiments, a mobile operating system 470 (e.g., iOS™, Android™, Windows Phone™, etc.) and one or more applications 480 may be loaded into the memory 460 from the storage 490 in order to be executed by the CPU 440. The applications 480 may include a browser or any other suitable mobile apps for receiving and rendering information respect to data processing or other information from the processing engine 130. User interactions with the information stream may be achieved via the I/O 450 and provided to the processing engine 130 and/or other components of the imaging system 100 via the network 140.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or external device. A computer may also act as a server if appropriately programmed.

Figure 5:
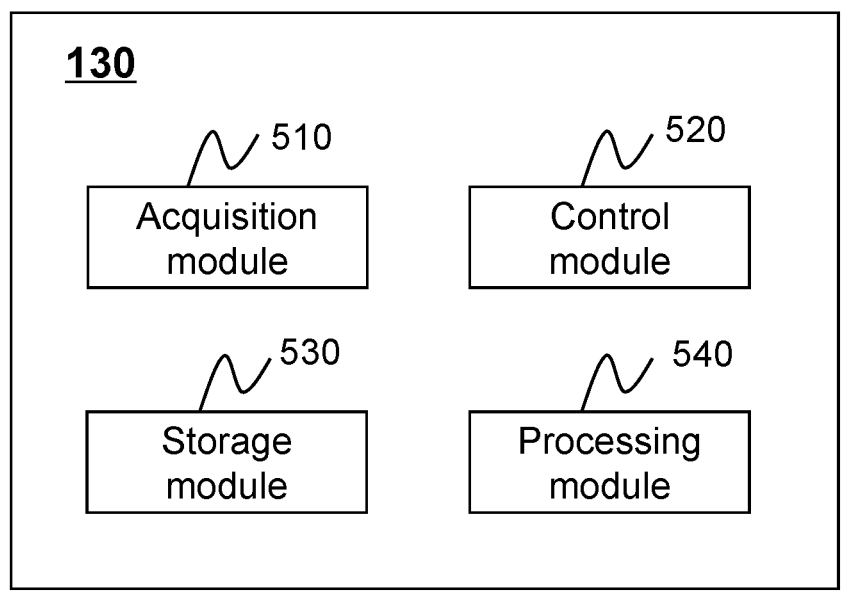
FIG. 5 is a block diagram illustrating an exemplary processing engine according to some embodiments of the present disclosure.

FIG. 5 is a block diagram illustrating an exemplary processing engine according to some embodiments of the present disclosure. The processing engine 130 may include an acquisition module 510, a control module 520, a storage module 530, and a processing module 540. In some embodiments, the acquisition module 510, the control module 520, the storage module 530, and/or the processing module 540 may be connected to and/or communicate with each other via a wired connection, a wireless connection, or any combination thereof.

The acquisition module 510 may acquire data. In some embodiments, the data may be acquired from the MR scanner 110, the examining table 120, the storage device 150, and/or the terminal device 160. In some embodiments, the data may include a scanning protocol, at least one portion of imaging gradient parameters as described elsewhere in the present disclosure, image data (e.g., encoded MR signals), instructions, or the like, or any combination thereof. The instructions may be executed by the processor(s) of the processing engine 130 to perform exemplary methods described in the present disclosure. In some embodiments, the acquired data may be transmitted the processing module 540 for further processing, or stored in the storage module 530.

The control module 520 may control operations of the acquisition module 510, the examining table 120, the storage module 530, and/or the processing module 540 (e.g., by generating one or more control parameters). For example, the control module 520 may control the acquisition module 510 to acquire data. As another example, the control module 520 may control the movement of the examining table 120.

As still another example, the control module 520 may control the processing module 540 to process a scanning protocol for determining one or more imaging gradient parameters. In some embodiments, the control module 520 may receive a real-time command or retrieve a predetermined command provided by a user (e.g., a doctor) to control one or more operations of the acquisition module 510 and/or the processing module 540. For example, the control module 520 may adjust the acquisition module 510 and/or the processing module 540 to generate image data associated with the MR signals according to the real-time command and/or the predetermined command. In some embodiments, the control module 520 may communicate with one or more other modules of the processing engine 130 for exchanging information and/or data.

The storage module 530 may store imaging gradient parameters, processed data, instructions, or the like, or any combination thereof. In some embodiments, the storage module 530 may store one or more scanning protocols, portion of imaging gradient parameters and/or encoded MR signals. In some embodiments, the storage module 530 may store program(s) and/or instruction(s) that can be executed by the processor(s) of the processing engine 130 to acquire data, determine imaging gradient parameters, reconstruct an image based on the imaging gradient parameters, and/or display any intermediate result or a resultant image.

The processing module 540 may process data provided by various modules of the processing engine 130. In some embodiments, the processing module 540 may process MR signals for reconstructing an MR image acquired by the acquisition module 510, retrieved from the storage module 530 and/or the storage device 150, etc. In some embodiments, the processing module 540 may determine and/or adjust at least one portion of imaging gradient parameters, such as a flow sensitive gradient based on other imaging gradient parameters.

In some embodiments, one or more modules illustrated in FIG. 5 may be implemented in at least part of the exemplary imaging system 100 as illustrated in FIG. 1. For example, the acquisition module 510, the control module 520, the storage module 530, and/or the processing module 540 may be integrated into a console (not shown). Via the console, a user may set parameters for scanning a subject, controlling imaging processes, controlling parameters for reconstruction of an image, visualizing a virtual scene associated with the subject, etc. In some embodiments, the console may be implemented via the processing engine 130 and/or the terminal device 160.

Figure 6:
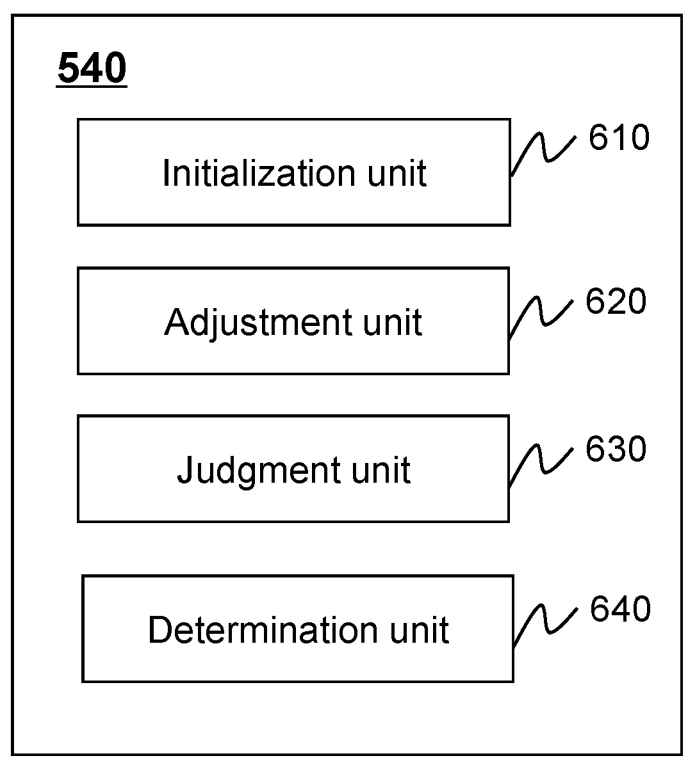
FIG. 6 is a block diagram illustrating an exemplary processing module according to some embodiments of the present disclosure.

FIG. 6 is a block diagram illustrating an exemplary processing module according to some embodiments of the present disclosure. As shown, the processing module 540 may include an initialization unit 610, an adjustment unit 620, a judgment unit 630, and a determination unit 640. In some embodiments, the initialization unit 610, the adjustment unit 620, the judgment unit 630, and/or the determination unit 640 may be connected to and/or communicate with each other via a wired connection, a wireless connection, or any combination thereof.

The initialization unit 610 may set an initial value to one or more imaging gradient parameters according to a scanning protocol. In some embodiments, the initialization unit 610 may initialize at least one duration and at least one amplitude value of at least one flow sensitive gradient. For example, if the flow sensitive gradient block has two flow sensitive gradients, for example, a first flow sensitive gradient and a second flow sensitive gradient, the initialization unit 610 may initialize a first duration t1 and a first amplitude value G1 of the first flow sensitive gradient, and a second duration t2 and a second amplitude value G2 of the second flow sensitive gradient.

The adjustment unit 620 may adjust at least one parameter of the pulse sequence. For example, one or more flow sensitive gradient block may be added to at least one imaging gradient direction (e.g., a phase encoding (PE) gradient, a readout (RO) gradient, a slice selecting encoding (SPE) gradient, etc.). Then, the imaging gradient parameter may be adjusted based on the parameter of the flow sensitive gradient block. In some embodiments, one or more parameters (e.g., a duration, an amplitude value, etc.) of the flow sensitive gradient block may be adjusted in a process for determining the flow sensitive gradient block.

The judgment unit 630 may perform a judgment function in a process for determining a flow sensitive gradient block. In some embodiments, the judgment unit 630 may determine that whether the flow sensitive gradient block is in accordance with a target condition. For example, the judgment unit 630 may determine that whether the zeroth-order gradient moment or the first-order gradient moment associated with the flow sensitive gradient block is in accordance with a target value, such as "0". As another example, the judgment unit 630 may determine that whether an amplitude value of a flow sensitive gradient is equal to or less than a threshold. In some embodiments, the target condition may be determined based on functions of the flow sensitive gradient block, such as flow encoding, flow compensation, flow dephasing, etc.

The determination unit 640 may determine one or more parameters related to a flow sensitive gradient block. In some embodiments, the parameters related to the flow sensitive gradient block may be determined based on other imaging gradient parameters, such as the parameters related to the phase encoding (PE) gradient, the readout (RO) gradient, the slice selecting encoding (SPE) gradient, etc.

This description is intended to be illustrative, and not to limit the scope of the present disclosure. Many alternatives, modifications, and variations will be apparent to those skilled in the art. The features, structures, methods, and characteristics of the exemplary embodiments described herein may be combined in various ways to obtain additional and/or alternative exemplary embodiments. For example, the adjustment unit 620 and the determination unit 640 may be integrated into one single unit. However, those variations and modifications do not depart the scope of the present disclosure.

Figure 7:
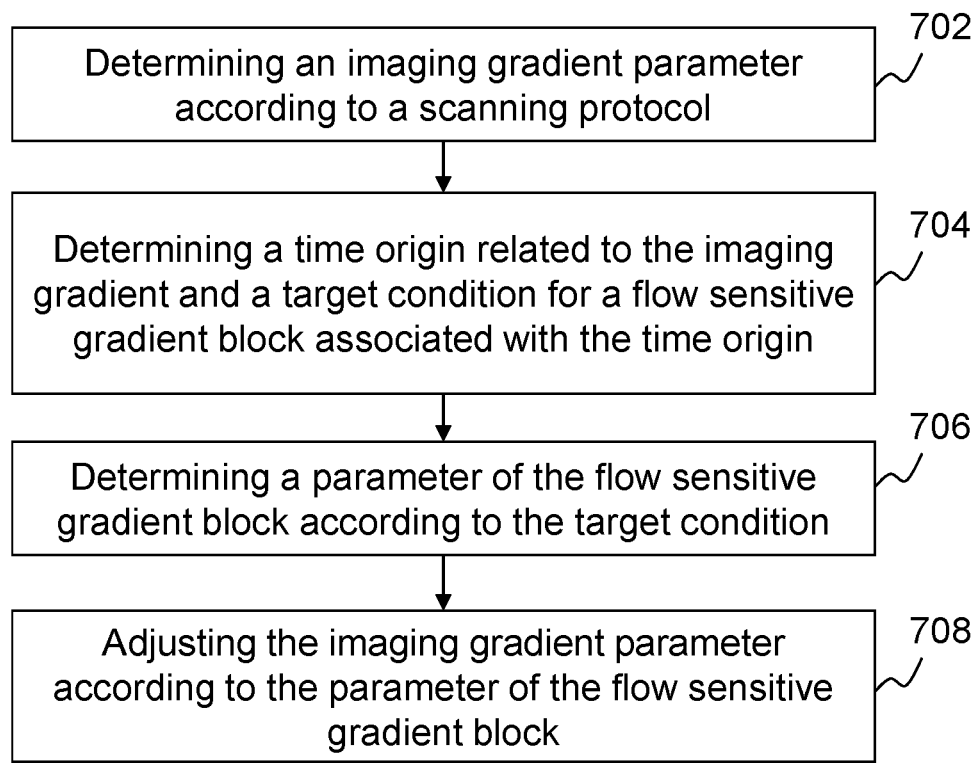
FIG. 7 is a flowchart illustrating an exemplary process for determining a flow sensitive gradient block according to some embodiments of the present disclosure.

FIG. 7 is a flowchart illustrating an exemplary process for determining a flow sensitive gradient block according to some embodiments of the present disclosure. The process 700 may be executed by the imaging system 100. For example, the process 700 may be implemented as a set of instructions (e.g., an application) stored in storage device 150 and/or storage module 530 in the processing engine 130. The processing engine 130 may execute the set of instructions and may accordingly be directed to perform the process 700 in the imaging system 100.

In 702, the processing engine 130 may determine an imaging gradient parameter according to a scanning protocol. The scanning protocol may be developed for various diseases and clinical scenarios. For example, the scanning protocol may be determined (or chosen) according to different subject or regions including head, brain, neck, body, shoulder, arm, thorax, cardiac, stomach, blood vessel, soft tissue, knee, feet, or the like, or any combination thereof. As another example, the scanning protocol may be an adult protocol, pediatric protocol, or animal protocol, etc. In some embodiments, the scanning protocol may be associated with a signal modality imaging device and/or a multi-modalities imaging device and include, for example, an MRI protocol, a PET-MRI protocol, a PET-CT protocol, etc. In some embodiments, the scanning protocol may be a standard protocol preinstalled in the imaging system 100. In some other embodiments, the scanning protocol may also be modified, revised, deleted, added, and/or updated by a user. The scanning protocol may be stored in the storage device 150 and/or the processing engine 130.

In some embodiments, the scanning protocol may have features including, for example, a weighted imaging method, a pulse sequence mode, a slice thickness, an inter-slice gap, a field of view (FOV), a scanning range, or the like, or any combination thereof. The weighted imaging method may be, for example, T1-weighted imaging (T1WI), T2-weighted imaging (T2WI), proton-density-weighted imaging (PDWI), T2*-weighted imaging (T2*WI), diffusion-weighted imaging (DWI), or the like, or any combination thereof. The pulse sequence mode may include, for example, a free induction decay (FID) sequence, a spin echo (SE) sequence, a fast spin echo (FSE) sequence (or turbo spin echo (TSE) sequence, rapid acquisition with relaxation enhancement (RARE) sequence, etc.), an inversion recovery (IR) sequence, a gradient recalled echo (GRE) sequence, a fast imaging with steady-state precession (FISP) sequence, or the like, or any combination thereof. The slice thickness may be the thickness of an excitation slice including, for example, 1 micrometer, 2 micrometers, 3 micrometers, or any other suitable values. The inter-slice thickness may be the thickness of the gap between two adjacent slices including, for example, 0 micrometer, 0.5 micrometer, 1 micrometer, or any other suitable values. The FOV may be associated with the area of the scanning captured, for example, 20 centimeters×20 centimeters, 20 centimeters×30 centimeters, or any other suitable values. The scanning range may be a region of a subject to be scanned, for example, an entire brain, a half breast, a left arm, or the like, or any combination thereof.

In some embodiments, the pulse sequence determined by the scanning protocol may include, for example, an RF pulse, an imaging gradient direction, and an MR signal. The gradient field may include a slice selecting gradient, a phase encoding gradient, and/or a readout gradient. Merely by way of example, the pulse sequence may be described as an exemplary diagram in FIG. 10-A. As illustrated in FIG. 10-A, the pulse sequence may include several components displayed in several sequence axes. The sequence axes may include an RF pulse axis, a slice selecting axis, a phase encoding axis, a readout axis, and an analog-to-digital converter (ADC) axis (not shown). In some other embodiments, the time sequence axes may be modified by, for example, adding an MR signal axis and/or deleting a phase encoding axis.

In some embodiments, the processing engine 130 may determine a parameter of the imaging gradient based on the scanning protocol. The parameter of the imaging gradient may include a repetition time (TR), an echo time (TE), a duration and/or an amplitude value of slice selecting gradient $G_{rf}$, a duration and/or an amplitude value of a readout gradient $G_{ro}$, or the like, or any combination thereof. For example, when excites a desired slice, a slice selecting gradient $G_{rf}$ may be imposed along a direction perpendicular to the plane of the desired slice simultaneously with the RF pulse. TE may be associated with time from the center of the RF pulse to the center of an echo. For pulse sequence with multi-echoes, several echo times may be defined and noted as $TE_1$, $TE_2$, $TE_3$, ..., $TE_n$, where n may be a positive integer.

In 704, the processing engine 130 may determine a time origin related to the imaging gradient and a target condition for a flow sensitive gradient block associated with the time origin. The time origin may be zero time used for gradient moment calculation, for example, determining a zeroth-order gradient moment M0 and/or a first-order gradient moment M1 as described elsewhere in the present disclosure. In some embodiments, the time origin may be determined according to the center of an echo. For example, as illustrated in FIG. 10-A, the center of an echo (e.g., $TE_1$, $TE_2$, $TE_3$, ..., $TE_n$) may be selected as the time origin, and noted as t=0. When TE is selected as the time origin, every time point before the center of the echo may have a negative value. As another example, any time point in the pulse sequence may be designated as the time origin according to different scenarios. It should be noted that the selection of the time origin does not affect the imaging gradient and the performance of the process 700 in the present disclosure.

In some embodiments, in 704, the processing engine 130 may also determine a target condition for a flow sensitive gradient block associated with the time origin. The flow sensitive gradient block may be a gradient portion added into the imaging gradient in the FIG. 10-A and/or FIG. 11-A. As illustrated in FIG. 10-A and/or FIG. 11-A, a gradient portion corresponding to a duration T before the readout gradient in the pulse sequence may be used to design the flow sensitive gradient block. In some embodiments, the flow sensitive gradient block may include at least one flow sensitive gradient. The shape of the flow sensitive gradient may include an echelon, a rectangle, a square, an arch, an irregular shape, or the like, or any combination thereof. Merely by way of example, the flow sensitive gradient may have a shape of echelon as shown in FIG. 10-B, FIG. 11-B, and FIG. 12.

In some embodiments, for a spin position r locating in a spin coordinate system having a center frequency consistent with a Larmor frequency. The Larmor frequency may be associated with the main magnetic field strength. In some embodiments, the spin position r may be a function of time t described as:

$$r(t) = r_0 + vt \quad (1),$$

where v represents a velocity assumed to be constant, and $r_0$ represents an initial position at the time origin (e.g., t=0).

In some embodiments, when imposed by the flow sensitive gradient having an amplitude value of G by a time period 0-τ, the spin position r may generate a phase described as:

$$\varphi(\tau) = -\gamma \int_0^\tau G(t) r(t) dt = -\gamma r_0 \int_0^\tau G(t) dt - \gamma v \int_0^\tau G(t) t dt \quad (2),$$

where γ represents a gyromagnetic ratio.

In some embodiments, a zeroth-order (0th) moment M0 and a first order (1st) moment M1 of the flow sensitive gradient may be described as:

$$M0 = \int_0^\tau G(t) dt \quad (3),$$

$$M1 = \int_0^\tau G(t) t dt \quad (4).$$

In some embodiments, the determination of the target condition for the flow sensitive gradient block may include designating M0 and/or M1 as $M_{0\text{-}target}$ and/or $M_{1\text{-}target}$. Merely by way of example, the target condition may be $M_{0\text{-}target} = 0$ and/or $M_{1\text{-}arget} = 0$ at the time origin.

In 706, the processing engine 130 may determine a parameter of the flow sensitive gradient block according to the target condition. In some embodiments, the parameter of the flow sensitive gradient block may include at least one duration and at least one amplitude value of the at least one flow sensitive gradient. For example, if the flow sensitive gradient block has two flow sensitive gradients (e.g., a first flow sensitive gradient P1 and a second flow sensitive gradient P2 as shown in FIG. 10-B), the processing engine 130 may determine a first duration t1 and a first amplitude value G1 of the first flow sensitive gradient, as well as a second duration t2 and a second amplitude value G2 of the second flow sensitive gradient. In some embodiments, t1, t2, G1, and G2 may be determined according to the target condition $M_{0\text{-}target}$ and/or $M_{1\text{-}target}$, based, for example, on the formula (3) and/or (4). In some embodiments, the sum of t1 and t2 may be equal to the duration T of the flow sensitive gradient block.

In some embodiments, in 706, the processing engine 130 may iteratively calculate or compute the parameter of the flow sensitive gradient block. Merely by way of example, the parameter may be adjusted or changed one or more times to match the target condition, as described in, for example, FIG. 8 or 9 and the description thereof.

In 708, the processing engine 130 may adjust the imaging gradient parameter according to the parameter of the flow sensitive gradient block. In some embodiments, when the parameter of the flow sensitive gradient block is determined, the parameter of the imaging gradient may be adjusted accordingly. The parameter of the imaging gradient may include, for example, a repetition time (TR), an echo time (TE), a starting time of slice selecting gradient $G_{rf}$, a starting time of a readout gradient $G_{ro}$. In some embodiments, the flow sensitive gradient block may be inserted into the pulse sequence to generate an adjusted pulse sequence as illustrated in FIG. 10-B and/or FIG. 11-B.

Figure 8:
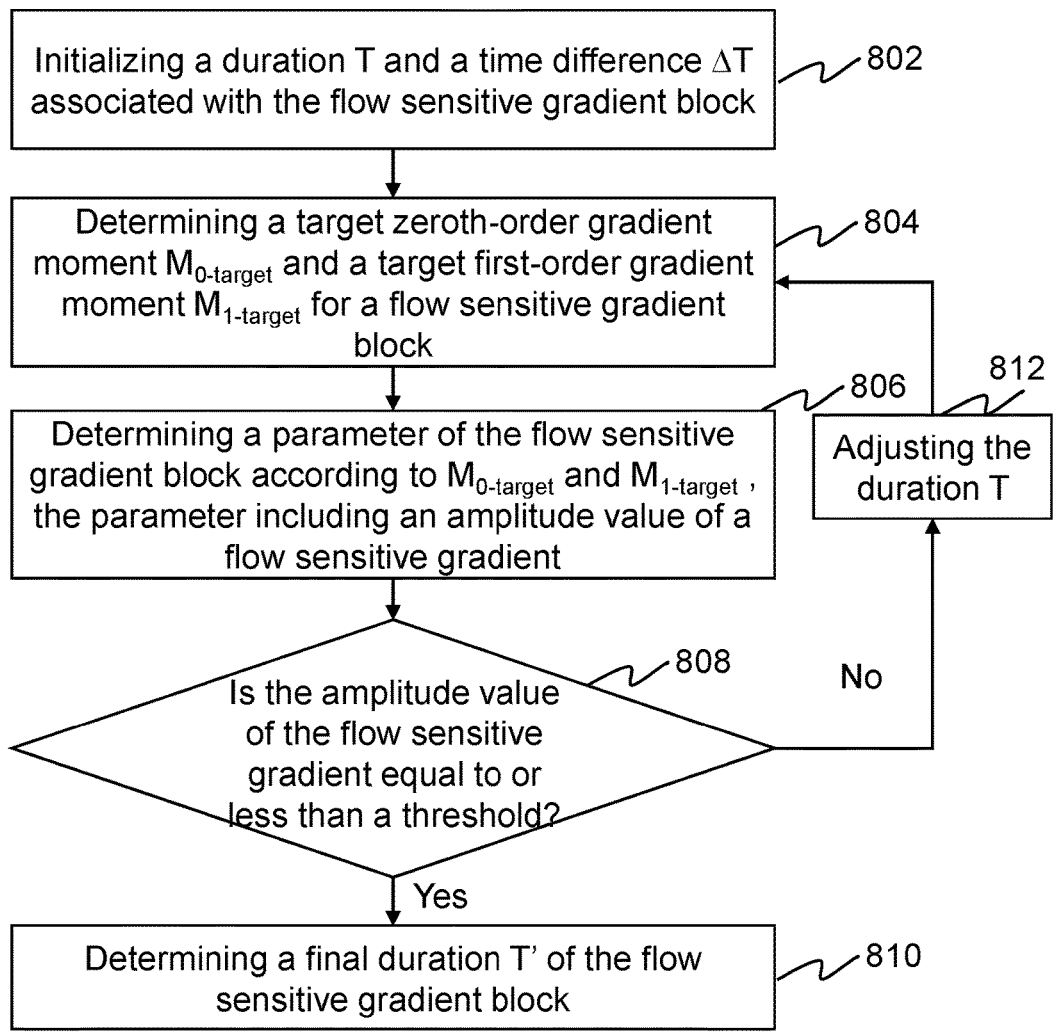
FIG. 8 is a flowchart illustrating an exemplary process for determining a flow sensitive gradient block according to some embodiments of the present disclosure.

FIG. 8 is a flowchart illustrating an exemplary process for determining a flow sensitive gradient block according to some embodiments of the present disclosure. The process 800 may be executed by the imaging system 100. For example, the process 800 may be implemented as a set of instructions (e.g., an application) stored in storage device 150 and/or storage module 530 in the processing engine 130. The processing engine 130 may execute the set of instructions and may accordingly be directed to perform the process 800 in the imaging system 100.

In 802, the processing engine 130 may initialize a duration T and a time difference ΔT associated with the flow sensitive gradient block. As illustrated in 706, the duration T of the flow sensitive gradient block may be determined. In some embodiments, the duration T may be a value, for example, doubling a rise time of the imaging gradient. Then the time difference ΔT associated with the flow sensitive gradient block may be determined accordingly. For example, the time difference ΔT may be a distance between the time origin (t=0) and a time point of the flow sensitive gradient block as shown in FIG. 10-A or FIG. 11-A. The time point may be at any position of the flow sensitive gradient block, merely by way of example, the time point may be an ending time.

In 804, the processing engine 130 may determine a target zeroth-order gradient moment $M_{0\text{-}target}$ and a target first-order gradient moment $M_{1\text{-}target}$ associated with the flow sensitive gradient block. In some embodiments, as shown in FIG. 10-B and/or FIG. 11-B, the target zeroth-order gradient moment $M_{0\text{-}target}$ and the target first-order gradient moment $M_{1\text{-}target}$ associated with the slice selecting axis, the phase encoding axis, and the readout axis may be the same or different. Merely by way of example, in the slice selecting axis, the target zeroth-order gradient moment $M_{0\text{-}target}$ may be the sum of zeroth-order gradient moment associated with a rephrase gradient of the slice selecting gradient $G_{rf}$ and zeroth-order gradient moment demanded by a present slice selecting phase encoding steps. The target first-order gradient moment $M_{1\text{-}target}$ may be a negative value of first-order gradient moment among $TE_1$ associated with the slice selecting gradient $G_{rf}$ from the center of the RF pulse to the ending time of the slice selecting gradient $G_{rf}$. As another example, in the phase encoding axis, the target zeroth-order gradient moment $M_{0\text{-}target}$ may be zeroth-order gradient moment demanded by present phase encoding steps. The target first-order gradient moment $M_{1\text{-}target}$ may be zero. As still another example, in the readout axis, the target zeroth-order gradient moment $M_{0\text{-}target}$ may be zeroth-order gradient moment associated with a prephrase gradient of the readout gradient $G_{ro}$. For example, the target zeroth-order gradient moment $M_{0\text{-}target}$ may be a negative value of zeroth-order gradient moment among $TE_1$ of the readout gradient $G_{ro}$ before $TE_1$. The target first-order gradient moment $M_{1\text{-}target}$ may be a negative value of first-order gradient moment among $TE_1$ of the readout gradient $G_{ro}$ before $TE_1$.

In some embodiments, a moment higher than the second order (e.g., M2, M3, M4, . . . , etc.) of the imaging gradient may be used to perform the process 800 according to the present disclosure.

In 806, the processing engine 130 may determine a parameter of the flow sensitive gradient block according to the $M_{0\text{-}target}$ and $M_{1\text{-}target}$. In some embodiments, the parameter of the flow sensitive gradient block may include at least one duration and at least one amplitude value of the at least one flow sensitive gradient. Merely by way of, as shown in FIG. 10-B, if the flow sensitive gradient block has two flow sensitive gradients (e.g., a first flow sensitive gradient P1 and a second flow sensitive gradient P2 on the SPE axis, the PE axis, and/or the RO axis), the processing engine 130 may determine a first duration t1 and a first amplitude value G1 of the first flow sensitive gradient, a second duration t2 and a second amplitude value G2 of the second flow sensitive gradient.

In some embodiments, the sum of t1 and t2 may be equal to the duration T of the flow sensitive gradient block. Given the duration T of the flow sensitive gradient block is stationary, t1 and t2 may be adjusted dynamically. In some embodiments, when at least one pair of t1 and t2 meet the demand target condition (e.g., $M_{0\text{-}target}$ and $M_{1\text{-}target}$) is required, the processing engine 130 may determine the first amplitude value G1 of the first flow sensitive gradient, the second amplitude value G2 of the second flow sensitive gradient, based on the formula (3) and/or (4).

In 808, the processing engine 130 may determine whether the amplitude value of the flow sensitive gradient is equal to or less than a threshold. In some embodiments, the threshold may be a value, a range, a formula, an order, or the like, or any combination thereof. Merely by way of example, the threshold may be associated with a maximum gradient of the imaging system 100. If the amplitude value of the flow sensitive gradient (e.g., G1, G2, etc.) is equal to or less than the threshold, the process 800 may proceed to 810. If the amplitude value of the flow sensitive gradient (e.g., G1, G2, etc.) is greater than the threshold, the process 800 may proceed to 812.

In 812, the processing engine 130 may adjust the duration T. Merely by way of example, the processing engine 130 may increase or decrease the duration T by using an adjusting value. For example, the duration T may be increased by the adjusting value to generate an adjusted duration T. As another example, the duration T may be changed by multiplying an adjusting coefficient including, for example, 0.6, 0.8, 1.0, 1.2, 1.4, . . . , etc.

After 812, the process may proceed to 804 to determine a target zeroth-order gradient moment $M_{0\text{-}target}$ and a target first-order gradient moment $M_{1\text{-}target}$ associated with the flow sensitive gradient block. In some embodiments, when the duration T is adjusted, the echo time TE (e.g., $TE_1$, $TE_2$, $TE_3$, . . . , $TE_n$) may be changed accordingly. Thus the target zeroth-order gradient moment $M_{0\text{-}target}$ and the target first moment $M_{1\text{-}target}$ may be re-determined based on the echo time TE (e.g., $TE_1$, $TE_2$, $TE_3$, . . . , $TE_n$).

In 810, the processing engine 130 may determine the duration T as a final duration T' (or a shared duration T') of the flow sensitive gradient block. In some embodiments, the process 800 may be executed on the slice selecting axis, the phase encoding axis, and the readout axis independently. For example, the processing engine 130 may determine a final duration Ts' (or an optimal duration Ts') associated with slice selecting axis, a final duration Tp' (or an optimal duration Tp') associated with the phase encoding axis, and a final duration Tr' (or an optimal duration Tr') associated with the readout coordinate axis. In some embodiments, the processing engine 130 may select a maximum of Tr', Tp', and Ts' as the final duration T' (or the shared duration T').

In some embodiments, when the final duration T' (the shared duration T') is determined in 810, the parameter of the imaging gradient including, for example, a repetition time (TR), an echo time (TE), a staring time of slice selecting gradient $G_{rf}$, a starting time of a readout gradient $G_{ro}$ may be adjusted accordingly. In some embodiments, the flow sensitive gradient block (t1, G1, t2, G2) may be inserted into the pulse sequence to generate an adjusted pulse sequence as illustrated in FIG. 10-B.

In some embodiments, the flow sensitive gradient block may be bipolar, for example, including at least two flow sensitive gradients associated with a double-pulse field gradient, G1=−G2. In some embodiments, the flow sensitive gradient block may be monopolar, for example, including one flow sensitive gradient associated with a single-pulse field gradient, G1=G, t1=T, G2=0, and t2=0. The embodiments may also be performed by process 800 as described in FIG. 10-A and FIG. 10-B in the present disclosure.

In some embodiments, the processing engine 130 may determine a flow sensitive gradient block as illustrated in FIG. 11-A and FIG. 11-B. As shown in FIG. 10-A, the pulse sequence may include two echoes, for example, a first echo and a second echo. In some embodiments, there may be a first flow sensitive gradient block associated with the first echo and a second flow sensitive gradient block associated with the second echo. The first flow sensitive gradient block and/or the second flow sensitive gradient block may be determined according to the process 700 or 800. For example, the processing engine 130 may determine the first flow sensitive gradient block according to the description elsewhere in the FIGS. 10-A and 10-B.

As another example, the processing engine 130 may determine the second flow sensitive gradient block based on the first flow sensitive gradient block. In some embodiments, a new readout gradient $G_{ro}'$ may be inserted according to the first flow sensitive gradient block. For example, $G_{ro}'$ may have a consistent direction with $G_{ro}$, which can be called a monopolar readout mode. As another example, $G_{ro}'$ may have an opposite direction compared with $G_{ro}$, which can be called a bipolar readout mode. The processing engine 130 may re-determine the echo time of the second echo $TE_2$ as a new time origin, and the duration T of the second flow sensitive gradient block. In some embodiments, the duration T may be a value, for example, doubling a rise time of the imaging gradient. Then the time difference ΔT associated with the second flow sensitive gradient block may be determined accordingly. For example, the time difference ΔT may be a distance between the new time origin (t=0) and a time point (e.g., an ending time) of the second flow sensitive gradient block (or a starting time of the new readout gradient $G_{ro}$') as shown in FIG. 11-A or FIG. 11-B.

The processing engine 130 may determine a target zeroth-order gradient moment $M_{0\text{-}target}$ and a target first-order gradient moment $M_{1\text{-}target}$ associated with the second flow sensitive gradient block. In some embodiments, the target zeroth-order gradient moment $M_{0\text{-}target}$ and the target first-order gradient moment $M_{1\text{-}target}$ associated with the slice selecting axis, the phase encoding axis, and the readout axis may be the same or different. Merely by way of example, as shown in FIG. 11-A, in the slice selecting axis and/or phase encoding axis, the target zeroth-order gradient moment $M_{0\text{-}target}$ may be zero. The target first-order gradient moment $M_{1\text{-}target}$ may be a negative value of first-order gradient moment among $TE_2$ associated with flow sensitive gradient G1, G2, and/or readout gradient $G_{ro}$ before the center of the second echo. As still another example, in the readout axis, the target zeroth-order gradient moment $M_{0\text{-}target}$ may be may be a negative value of the sum of zeroth-order gradient moment of the readout gradient $G_{ro}$ and the new readout gradient $G_{ro}$' between $TE_1$ and $TE_2$. The target first-order gradient moment $M_{1\text{-}target}$ may be a negative value of first-order gradient moment among $TE_2$ of the readout gradient $G_{ro}$ and/or the new readout gradient $G_{ro}$' between $TE_1$ and $TE_2$.

In some embodiments, a moment more than second order (e.g., M2, M3, M4, . . . , etc.) of the imaging gradient and/or the flow sensitive gradient may be used to determine the flow sensitive gradient block.

In some embodiments, the processing engine 130 may determine a parameter of the second flow sensitive gradient block including, for example, at least one duration and at least one amplitude value of the at least one flow sensitive gradient. Merely by way of, as shown in FIG. 11-B, if the second flow sensitive gradient block has two flow sensitive gradients (e.g., a first flow sensitive gradient P1 and a second flow sensitive gradient P2 on the SPE axis, the PE axis, and/or the RO(bi) axis), the processing engine 130 may determine a first duration t1 and a first amplitude value G1 of the first flow sensitive gradient, as well as a second duration t2 and a second amplitude value G2 of the second flow sensitive gradient.

In some embodiments, the sum of t1 and t2 may be equal to the duration T of the flow sensitive gradient block. Given the duration T of the flow sensitive gradient block is fixed, t1 and t2 may be adjusted dynamically. In some embodiments, when at least one pair of t1 and t2 meet the demand target condition (e.g., $M_{0\text{-}target}$ and $M_{1\text{-}target}$) is required, the processing engine 130 may determine the first amplitude value G1 of the first flow sensitive gradient, the second amplitude value G2 of the second flow sensitive gradient, based on the formula (3) and/or (4).

In some embodiments, the processing engine 130 may determine whether the amplitude value of the flow sensitive gradient is equal to or less than a threshold. In some embodiments, the threshold may be a value, a range, a formula, an order, or the like, or any combination thereof. Merely by way of example, the threshold may be associated with the maximum gradient of the imaging system 100. If the amplitude value of the flow sensitive gradient (e.g., G1, G2, etc.) is equal to or less than the threshold, the processing engine 130 may determine the duration T as a final duration T' of the second flow sensitive gradient block. If the amplitude value of the flow sensitive gradient (e.g., G1, G2, etc.) is greater than the threshold, the processing engine 130 may adjust the duration T. Merely by way of example, the processing engine 130 may increase or decrease the duration T by using an adjusting value. For example, the duration T may be increased by the adjusting value to generate an adjusted duration T. As another example, the duration T may be changed by multiplying an adjusting coefficient including, for example, 0.6, 0.8, 1.0, 1.2, 1.4, . . . , etc. In some embodiments, when the duration T is adjusted, the echo time TE (e.g., $TE_1$, $TE_2$, $TE_3$, . . . , $TE_n$) may be changed accordingly. Thus the target zeroth-order gradient moment $M_{0\text{-}target}$ and the target first-order gradient moment $M_{1\text{-}target}$ may be re-determined based on the changed or updated echo time TE (e.g., $TE_1$, $TE_2$, $TE_3$, . . . , $TE_n$).

In some embodiments, the second flow sensitive gradient block may be executed on the slice selecting axis, the phase encoding axis, and the readout axis independently as shown in FIG. 11-A or FIG. 11-B. For example, the processing engine 130 may determine a final duration Ts' (or an optimal duration Ts') associated with slice selecting axis, a final duration Tp' (or an optimal Tp') associated with the phase encoding axis, and a final duration Tr' (or an optimal duration Tr') associated with the readout coordinate axis. In some embodiments, the processing engine 130 may select the greatest duration among Tr', Tp', and Ts' as the final duration T' (or the shared duration T').

In some embodiments, when the final duration T' (or the shared duration T') is determined, the parameter of the imaging gradient including, for example, a repetition time (TR), an echo time ($TE_2$), and a starting time of a readout gradient $G_{ro}$' may be adjusted accordingly. In some embodiments, the second flow sensitive gradient block (t1, G1, t2, G2) may be inserted into the pulse sequence to generate an adjusted pulse sequence as illustrated in FIG. 11-B.

Figure 9:
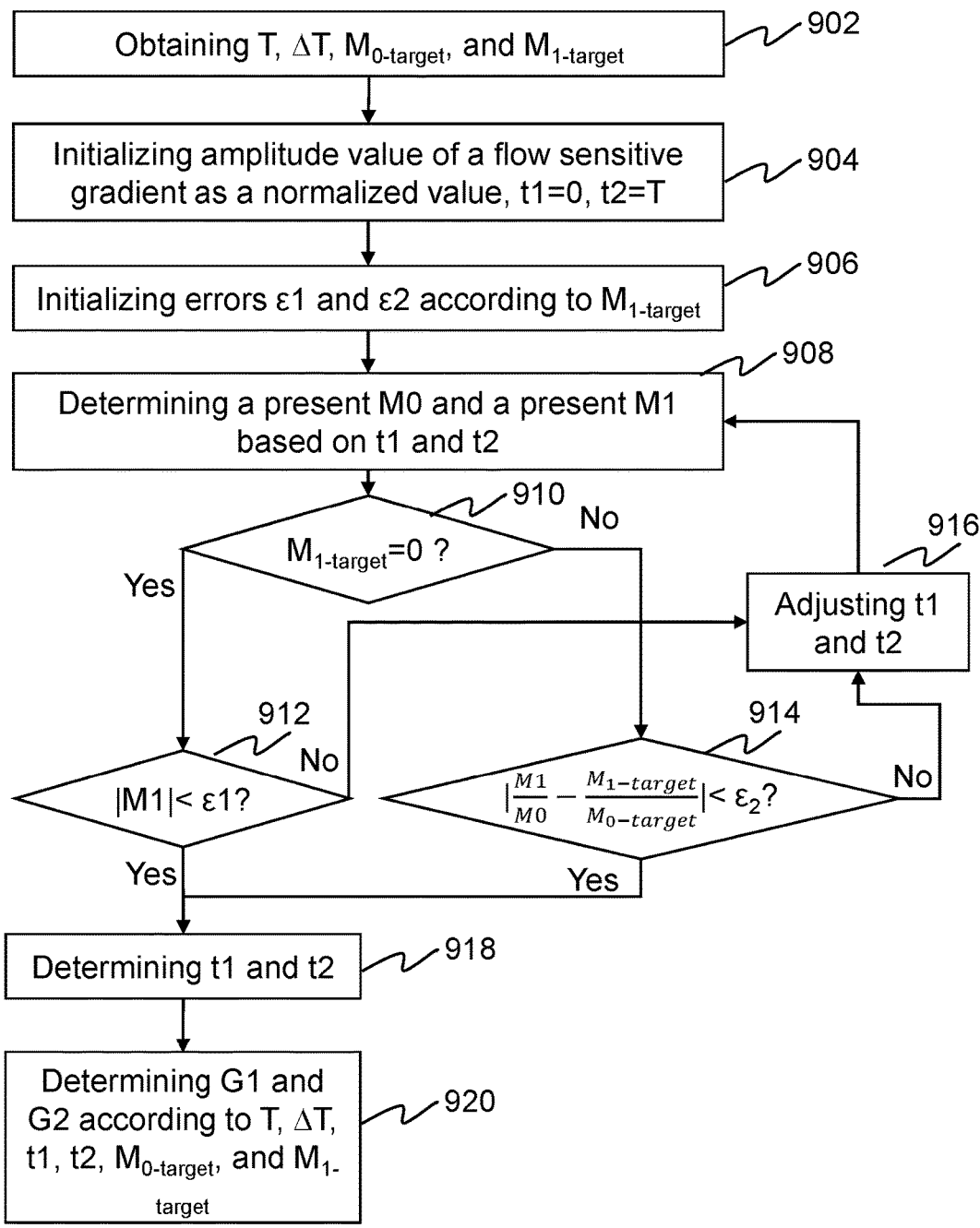
FIG. 9 is a flowchart illustrating an exemplary process for determining a flow sensitive gradient block according to some embodiments of the present disclosure.

FIG. 9 is a flowchart illustrating an exemplary process for determining a flow sensitive gradient block according to some embodiments of the present disclosure. The process 900 may be executed by the imaging system 100. For example, the process 900 may be implemented as a set of instructions (e.g., an application) stored in storage device 150 and/or storage module 530 in the processing engine 130. The processing engine 130 may execute the set of instructions and may accordingly be directed to perform process 900 in the imaging system 100.

In 902, the processing engine 130 may obtain a parameter of a flow sensitive gradient block. The parameter may include a duration T, a time difference ΔT, a target zeroth-order gradient moment $M_{0\text{-}target}$, and a target first-order gradient moment $M_{1\text{-}target}$ associated with a flow sensitive gradient block. In some embodiments, T, ΔT, $M_{0\text{-}target}$, and $M_{1\text{-}target}$ may be determined according to the description of step 802 and/or 804 in FIG. 8.

In 904, the processing engine 130 may initialize a parameter of the flow sensitive gradient block. In some embodiments, the processing engine 130 may initialize the amplitude value of the flow sensitive gradient block to be a normalized value. In some embodiments, the normalized value may be 1 or −1. For example, if the flow sensitive gradient block is bipolar, then the amplitude value G1 of the first flow sensitive gradient may be initialized to be 1 and the amplitude value G2 of the second flow sensitive gradient may be initialized to be −1. As another example, if the flow compensating module is monopolar, then G1 may be initialized to be 1 and G2 may be initialized to be zero, or G1 may be initialized to be zero and G2 may be initialized to be 1. In some embodiments, a first duration t1 of the first sensitive gradient and a second duration t2 of the second flow sensitive gradient may be initialized so that t1=0 and t2=T.

In 906, the processing engine 130 may initialize two error tolerance thresholds ε1 and ε2 according to $M_{1\text{-}target}$. For example, the error tolerance thresholds ε1 and ε2 may be set as values no more than $10^{-N}$, where N may be an integer.

In 908, the processing engine 130 may determine a present M0 and a present M1 based on the initialized t1, t2, G1, and G2. In some embodiments, the present M0 and the present M1 may be determined according to the formula (3) and/or (4) as described in connection with step 704 in FIG. 7.

In 910, the processing engine 130 may determine whether the target first-order gradient moment $M_{1\text{-}target}$ is equal to zero. If $M_{1\text{-}target}$ is equal to zero, the process 900 may proceed to 912. If $M_{1\text{-}target}$ is unequal to zero, the process 900 may proceed to 914.

In 912, the processing engine 130 may determine whether the absolute value of the present M1 is less than the error tolerance threshold ε1. If the absolute value of the present M1 is less than the error tolerance threshold ε1, the process 900 may proceed to 918. If the absolute value of the present M1 is not less than the error tolerance threshold ε1, the process 900 may proceed to 916.

In 914, the processing engine 130 may judge whether the difference between the relative ratio of the present M1 and the present M0 and the relative ratio of $M_{1\text{-}target}$ and $M_{0\text{-}target}$ (also referred to as $$\left|\frac{M1}{M0} - \frac{M_{1\text{-}target}}{M_{0\text{-}target}}\right|)$$

is less than the error tolerance threshold ε2. If the difference between the relative ratio of M1 and M0 and the relative ratio of $M_{1\text{-}target}$ and $M_{0\text{-}target}$ is less than the error tolerance threshold ε2, the process and/or method 900 may proceed to 918. If the difference between the relative ratio of M1 and M0 and the relative ratio of $M_{1\text{-}target}$ and $M_{0\text{-}target}$ is not less than the error tolerance threshold ε2, the process 900 may proceed to 916.

In 916, the processing engine 130 may adjust the duration t1 and t2. For example, the processing engine 130 may increase the duration t1 and decrease the duration t2 by a step length h. The adjusted t1 and t2 may still satisfy one or more restriction conditions. In some embodiments, the restriction conditions may include the sum of t1 and t2 is equal to T, t1 and t2 are both non-negative, and t1 and t2 are both no more than T. In some embodiments, the value of step length h may be determined pre-hand. For example, the step length h may be a value no more than $10^{-N}$, where N may be an integer. In some embodiments, the step length h may be fixed, or may be varying during each iteration.

In 918, the processing engine 130 may determine t1 and t2. In some embodiments, t1 and t2 in 918 may be the same as the initialized t1 and t2 in 904. In some embodiments, t1 and t2 in 918 may be different from the initialized t1 and t2 (e.g., t1 and t2 adjusted in 916).

In 920, the processing engine 130 may determine G1 and G2 according to T, ΔT, t1, t2, $M_{1\text{-}target}$ and $M_{0\text{-}target}$ according to the formula (3) and/or (4).

FIG. 10-A illustrates exemplary diagrams of a single echo pulse sequence according to some embodiment of the present disclosure. As shown in FIG. 10-A, the signal echo pulse sequence may include several components displayed in several sequence axes. The sequence axes may include an RF pulse axis, a slice selecting (SPE) axis, a phase encoding (PE) axis, and a readout (RO) axis, and an analog-to-digital converter (ADC) axis (not shown). A slice selecting gradient $G_{rf}$ and a readout gradient $G_{ro}$ may be inserted onto the SPE axis and the RO axis respectively. A flow sensitive gradient block may be inserted to the single echo pulse sequence. The flow sensitive gradient block may be used to perform a function of flow compensation, flow encoding, and/or flow dephasing. The duration T of the flow sensitive gradient block may be initialized to be a value. For example, the initial value of T may be chosen as twice the rising time of least imaging gradient of the imaging system 100. The center of an echo $TE_1$ (also referred to as echo time) may be selected as the time origin and noted as t=0. The center of the echo $TE_1$ may be determined based on the duration T of the flow sensitive gradient block. The time difference ΔT starting from the starting time of $G_{ro}$ while ending at $TE_1$ may be a fixed value, for example, the time difference ΔT may be the half-width of the readout gradient $G_{ro}$.

FIG. 10-B illustrates exemplary diagrams of a single echo pulse sequence with the flow sensitive gradient block according to some embodiment of the present disclosure. As shown in FIG. 10-B, the SPE axis, the PE axis, and the RO axis are respectively inserted by a flow sensitive gradient block. The flow sensitive gradient block may be bipolar on each axis, for example, including a first sensitive gradient P1 and a second sensitive gradient P2. The parameters (e.g., the amplitude value G1 and the duration t1 of the first flow sensitive gradient P1 and the amplitude value G2 and the duration t2 of the second flow sensitive gradient P2) of the flow sensitive gradient block on each axis may be determined based on the target zeroth-order gradient moment $M_{0\text{-}target}$ and the target first-order gradient moment $M_{1\text{-}target}$ at the time origin along the SPE axis, PE axis, and RO axis.

The target zeroth-order gradient moment $M_{0\text{-}target}$ and the target first-order gradient moment $M_{1\text{-}target}$ for the flow sensitive gradient block at the time origin along the SPE axis, PE axis, and RO axis may be calculated respectively. In the SPE axis, the target zeroth-order gradient moment $M_{0\text{-}target}$ may be the sum of zeroth-order gradient moment associated with a rephrase gradient of the slice selecting gradient $G_{rf}$ and zeroth-order gradient moment demanded by a present slice selecting phase encoding steps. The target first-order gradient moment $M_{1\text{-}target}$ may be the negative value of first-order gradient moment among $TE_1$ associated with the slice selecting gradient $G_{rf}$ from the center of the RF pulse to the ending time of the slice selecting gradient $G_{rf}$. In the PE axis, the target zeroth-order gradient moment $M_{0\text{-}target}$ may be zeroth-order gradient moment demanded by present phase encoding steps. The target first-order gradient moment $M_{1\text{-}target}$ may be zero. In the RO axis, the target zeroth-order gradient moment $M_{0\text{-}target}$ is a negative value of zeroth-order gradient moment among $TE_1$ of the readout gradient $G_{ro}$ before $TE_1$. The target first-order gradient moment $M_{1\text{-}target}$ is a negative value of first-order gradient moment among $TE_1$ of the readout gradient $G_{ro}$ before $TE_1$.

A minimum value Ts' associated with the SPE axis, a minimum value Tp' associated with the PE axis, and a minimum value Tr' associated with the RO axis may be determined independently according to the description as illustrated in FIG. 8. For each axis, in order to satisfy target zeroth-order gradient moment $M_{0\text{-}target}$ and target first-order gradient moment $M_{1\text{-}target}$, a smaller value of duration T may lead to a greater amplitude value of the flow sensitive gradient, which may exceed the maximum value of the amplitude value allowed by the imaging system 100. On the SPE axis, the duration T may be increased to determine a minimum value Ts' under which the amplitude value of the flow sensitive gradient is less than the maximum amplitude value that is allowed by the imaging system 100. Likewise, the minimum value Tp' associated with the PE axis and the minimum value Tr' associated with the RO axis may be determined. The amplitude values of the flow sensitive gradient along the PE axis and the RO axis may be less than the maximum amplitude value that is allowed by the imaging system 100.

Then a maximum of Tr', Tp', and Ts' may be defined as the final duration T' (or the shared duration T') for the PE axis, the RO axis, and the RO axis. For the final duration T', the amplitude value of the flow sensitive gradient may be calculated according to the description as illustrated in FIG. 9. The amplitude value of the flow sensitive gradient may meet the requirement for the target zeroth-order gradient moment $M_{0\text{-}target}$ and the target first-order gradient moment $M_{1\text{-}target}$ along the SPE axis, PE axis, and RO axis.

FIG. 10-C illustrates exemplary diagrams of curves respecting to zeroth-order gradient moment M0 and first-order gradient moment M1 varied with time according to some embodiment of the present disclosure. As shown in FIG. 10-C, the zeroth-order gradient moment M0 and first-order gradient moment M1 may have been normalized for the purpose of analysis. At $TE_1$, on the SPE axis and the PE axis, the first-order gradient moment M1 may be zero, whereas the zeroth-order gradient moment M0 is the corresponding zeroth-order gradient moment demanded by present phase encoding steps on the SPE axis and the PE axis respectively. On the RO axis, the zeroth-order gradient moment M0 and the first-order gradient moment M1 are both zero at $TE_1$.

FIG. 11-A illustrates exemplary diagrams of a double echo pulse sequence according to some embodiments of the present disclosure. As shown in FIG. 11-A, the double echo pulse sequence may include several components displayed in several time sequence axes. The sequence axes may include an RF pulse axis, a slice selecting (SPE) axis, a phase encoding (PE) axis, a readout (RO) axis, and an analog-to-digital converter (ADC) axis (not shown). The double echo pulse sequence may include two flow sensitive gradient blocks, e.g., a first flow sensitive gradient and a second flow sensitive gradient. The first flow sensitive gradient blocks may be determined as described herein in connection with FIG. 10-A to FIG. 10-C. To determine the second flow sensitive gradient, a slice selecting gradient $G_{rf}$ and a readout gradient $G_{ro}$ may be inserted to the SPE axis and the RO axis respectively. In some embodiments, the readout gradient $G_{ro}$ may be associated with the feature of the first flow sensitive gradient block. For example, if the readout is in a monopolar mode, the new readout gradient $G_{ro}'$ may have a consistent direction with $G_{ro}$, as shown in RO(mono) axis of FIG. 11-A. As another example, if the readout is in a bipolar mode, the new readout gradient $G_{ro}'$ may have an opposite direction compared with $G_{ro}$, as shown in RO(bi) axis of FIG. 11-A. The flow sensitive gradient block may be used to perform a function of flow compensation, flow encoding, and/or flow dephasing. The duration T of the flow sensitive gradient block may be initialized to be a value. For example, the initial value of T may be chosen as twice the rising time of least imaging gradient of the imaging system 100. The center of an echo $TE_2$ may be selected as the time origin, and noted as t=0. The time difference $\Delta T$ starting from the starting time of $G_{ro}$ while ending at $TE_2$ may be a fixed value, for example, the time difference $\Delta T$ may be the half-width of the readout gradient $G_{ro}$.

FIG. 11-B illustrates exemplary diagrams of a double echo pulse sequence with the flow sensitive gradient block according to some embodiment of the present disclosure. As shown in FIG. 11-B, the SPE axis, the PE axis, and the RO axis are inserted by the second flow sensitive gradient block. In some embodiments, the second flow sensitive gradient block may be bipolar on each axis including, for example, a first flow sensitive gradient P1 and a second flow sensitive gradient P2. In some embodiments, the second flow sensitive gradient block may be monopolar on the RO axis, for example, including only one flow sensitive gradient. The parameters (e.g., the amplitude value G1 and the duration t1 of the first flow sensitive gradient P1 and the amplitude value G2 and the duration t2 of the second flow sensitive gradient P2) of the flow sensitive gradient block on each axis may be determined based on the target zeroth-order gradient moment $M_{0\text{-}target}$ and the target first-order gradient moment $M_{1\text{-}target}$ at the time origin along the SPE axis, PE axis, and RO axis.

The target zeroth-order gradient moment $M_{0\text{-}target}$ and the target first-order gradient moment $M_{1\text{-}target}$ for the flow sensitive gradient block at the time origin along the SPE axis, PE axis, and RO axis may be calculated respectively. In the slice selecting axis and/or phase encoding axis, the target zeroth-order gradient moment $M_{0\text{-}target}$ may be zero. The target first-order gradient moment $M_{1\text{-}target}$ may be a negative value of first-order gradient moment among $TE_2$ associated with flow sensitive gradient G1, G2, and/or readout gradient $G_{ro}$ before the center of the second echo. As still another example, in the readout axis, the target zeroth-order gradient moment $M_{0\text{-}target}$ may be a negative value of sum of zeroth-order gradient moment of the readout gradient $G_{ro}$ and the new readout gradient $G_{ro}'$ between $TE_1$ and $TE_2$. The target first-order gradient moment $M_{1\text{-}target}$ may be a negative value of first-order gradient moment among $TE_2$ of the readout gradient $G_{ro}$ and/or the new readout gradient $G_{ro}'$ between $TE_1$ and $TE_2$.

A minimum value Ts' associated with the SPE axis, a minimum value Tp' associated with the PE axis, and a minimum value Tr' associated with the RO axis may be determined independently according to the description as illustrated in FIG. 8. For each axis, a smaller value of duration T may lead to a greater amplitude value of the flow sensitive gradient, which may exceed the maximum value of the amplitude value allowed by the imaging system 100. On the SPE axis, the duration T may be increased to determine a minimum value Ts' under which the amplitude value of the flow sensitive gradient is less than the maximum amplitude value that is allowed by the imaging system 100. Likewise, the minimum value Tp' associated with the PE axis and the minimum value Tr' associated with the RO axis may be determined. The amplitude values of the flow sensitive gradient along the PE axis and the RO axis may be less than the maximum amplitude value that is allowed by the imaging system 100.

Then a maximum of Tr', Tp', and Ts' may be defined as the final duration T' (or the shared duration T') for the PE axis, the RO axis, and the RO axis. For the final duration T', the amplitude value of the flow sensitive gradient may be calculated according to the description as illustrated in FIG. 9. For example, a pair of t1 and t2 associated with a flow sensitive gradient block for each axis may be determined according to the final duration T'. Then, the first amplitude value G1 and the second amplitude value G2 of the flow sensitive gradient block for each axis may be determined based on the formula (3) and/or (4). The amplitude values G1 and G2 of the flow sensitive gradient block for each axis may keep the zeroth-order gradient moment and the first-order gradient moment of the flow sensitive gradient block for each axis in accordance with the target zeroth-order gradient moment $M_{0\text{-}target}$ and the target first-order gradient moment $M_{1\text{-}target}$ along the SPE axis, PE axis, and RO axis.

FIG. 11-C illustrates exemplary diagrams of curves respecting to zeroth-order gradient moment M0 and first-order gradient moment M1, which may vary with time according to some embodiments of the present disclosure. As shown in FIG. 11-C, the zeroth-order gradient moment M0 and first-order gradient moment M1 may have been normalized. At $TE_2$, on the SPE axis and the PE axis, their first-order gradient moment M1 are both zero. On the RO axis, the zeroth-order gradient moment M0 and the first-order gradient moment M1 are both zero at $TE_2$. In some embodiments, for the monopolar readout mode, its corresponding flow sensitive gradient block may be monopolar (as described in RO(mono-1) axis) and/or bipolar (as described in RO(mono-2) axis).

FIG. 12-A illustrates exemplary diagrams of a multi-echoes sequences according to some embodiments of the present disclosure. For example, the multi-echoes may include no less than three echoes (e.g., five echoes) as shown in FIG. 12-A. Each flow sensitive gradient block corresponding to each echo may be determined based on the process 800 and process 900 as described elsewhere in the present disclosure. Merely by way of example, a fifth flow sensitive gradient block associated with the fifth echo in FIG. 12-A may be described as below.

As shown in FIG. 12-B, the time origin for determining the fifth flow sensitive gradient may be $TE_5$. On the SPE axis and the PE axis, the first-order gradient moment M1 at $TE_5$ may be equal to zero, and the first-order gradient moment M1 on each TE before $TE_5$ may not be equal to zero. In the RO axis, the zeroth-order gradient moment M0 and first-order gradient moment M1 at each TE may be equal to zero. In some embodiments, for the monopolar readout mode, its corresponding flow sensitive gradient block may be monopolar (as described in RO(mono-1) axis) and/or bipolar (as described in RO(mono-2) axis).

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by the present disclosure, and are within the spirit and scope of the exemplary embodiments of the present disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as JAVA, SCALA, SMALLTALK, EIFFEL, JADE, EMERALD, C++, C#, VB. NET, PYTHON or the like, conventional procedural programming languages, such as the "C" programming language, VISUAL BASIC, FORTRAN 2013, PERL, COBOL 2012, PHP, ABAP, dynamic programming languages such as PYTHON, RUBY and BROOVY, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

I claim:

1. A system comprising:
at least one non-transitory computer-readable storage medium including a set of instructions;
at least one processor in communication with the at least one non-transitory computer-readable storage medium, wherein when executing the instructions, the at least one processor is configured to cause the system to:
determine an imaging gradient parameter according to a scanning protocol;
determine a time origin for gradient moment calculation and a target condition for a flow sensitive gradient block associated with the time origin;
determine a parameter of a flow sensitive gradient block according to the target condition, the flow sensitive gradient block including at least one flow sensitive gradient, the parameter of the flow sensitive gradient block including at least one duration and at least one amplitude value of the at least one flow sensitive gradient;
modify the parameter of the flow sensitive gradient block by adjusting a duration of the flow sensitive gradient block iteratively, wherein the duration of the flow sensitive gradient block is determined based on the at least one duration of the at least one flow sensitive gradient; and
adjusting the imaging gradient parameter by inserting the modified flow sensitive gradient block into the imaging gradient parameter.

2. The system of claim 1, wherein the flow sensitive gradient block further includes a first flow sensitive gradient and a second flow sensitive gradient.

3. The system of claim 1, wherein the target condition further includes a target zeroth-order gradient moment and a target first-order gradient moment associated with the flow sensitive gradient block.

4. The system of claim 2, wherein the at least one processor is further configured to cause the system to:
initialize a duration T and a time difference ΔT associated with the flow sensitive gradient block, the duration T being a time length of the flow sensitive gradient block, the time difference ΔT being a distance between the time origin and a time point of the flow sensitive gradient block.

5. The system of claim 4, wherein the at least one processor is further configured to cause the system to:
determine a first amplitude value of the first flow sensitive gradient and a second amplitude value of the second flow sensitive gradient;
determine the first amplitude value and the second amplitude value are equal to or less than a threshold; and
in response to the determination that the first amplitude value and the second amplitude value are equal to or less than the threshold, determine the current duration T as the duration of the flow sensitive gradient block.

6. The system of claim 5, wherein the at least one processor is further configured to cause the system to:
determine the first amplitude value and the second amplitude value are larger than the threshold; and
in response to the determination that the first amplitude value and the second amplitude value are larger than the threshold, adjusting the current duration T of the flow sensitive gradient block, wherein the adjusted duration T is designated as the duration of the flow sensitive gradient block in a next iterative operation.

7. The system of claim 5, wherein:
the parameter of the flow sensitive gradient block further includes a component on a slice selecting axis, a component on a phase encoding axis, and a component on a readout coordinate axis, and the at least one processor is further configured to cause the system to:
    determine a final duration Ts' associated with the slice selecting axis, a final duration Tp' associated with the phase encoding axis, and a final duration Tr' associated with the readout coordinate axis, respectively; and
    determine a shared duration T' for the slice selecting axis, the phase encoding axis, and the readout coordinate axis based on the final durations, wherein the shared duration T' is designated as the duration of flow sensitive gradient block.

8. The system of claim 1, wherein the scanning protocol is associated to a pulse sequence of one or more echoes.

9. The system of claim 1, wherein the flow sensitive gradient block is further used to perform at least one function of flow encoding, flow compensation, or flow dephasing.

10. The system of claim 7, wherein to determine a shared duration T' for the phase encoding axis slice selecting axis, the phase encoding axis, and the readout coordinate axis based on the final durations, the at least one processor is further configured to cause the system to:
    determine a maximum value of the final durations, Tr', Tp' and Ts', as the shared duration T'.

11. A method implemented on a computing device having at least one processor, at least one computer-readable storage medium, and a communication port connected to an imaging device, the method comprising:
    determining an imaging gradient parameter for an echo in an imaging sequence;
    determining a time origin for gradient moment calculation based on the imaging gradient parameter;
    obtaining at least a target zeroth-order gradient moment and a target first-order gradient moment corresponding to the time origin;
    determining a parameter of a flow sensitive gradient block with respect to the target zeroth-order gradient moment and the target first-order gradient moment, the flow sensitive gradient block including at least one flow sensitive gradient, the parameter of the flow sensitive gradient block including at least one duration and at least one amplitude value of the at least one flow sensitive gradient;
    modifying the parameter of the flow sensitive gradient block by adjusting a duration of the flow sensitive gradient block iteratively, wherein the duration of the flow sensitive gradient block is determined based on the at least one duration of the at least one flow sensitive gradient; and
    updating the imaging gradient parameter by inserting the modified flow sensitive gradient block into the imaging gradient parameter.

12. The method of claim 11, wherein the imaging sequence is a single-echo sequence, and the first flow sensitive gradient block comprising a single-pulse field gradient or a double-pulse field gradient.

13. The method of claim 12, wherein the flow sensitive gradient block includes a first sensitive gradient and a second sensitive gradient, further comprising:
    initializing a duration T and a time difference $\Delta T$ associated with the flow sensitive gradient block, the duration T being a time length of the flow sensitive gradient block, the time difference $\Delta T$ being a distance between the time origin and a time point of the flow sensitive gradient block.

14. The method of claim 13, further comprising:
    determining a first amplitude value of the first flow sensitive gradient and a second amplitude value of the second flow sensitive gradient;
    determining the first amplitude value and the second amplitude value equal to or less than a threshold; and
    in response to the determination that the first amplitude value and the second amplitude value are equal to or less than the threshold, determining the current duration T as the duration of the flow sensitive gradient block.

15. The method of claim 14, further comprising:
    determining the first amplitude value and the second amplitude value are larger than the threshold; and
    in response to the determination that the first amplitude value and the second amplitude value are larger than the threshold, adjusting the current duration T of the flow sensitive gradient block, wherein the adjusted duration T is designated as the duration of the flow sensitive gradient block in a next iterative operation.

16. The method of claim 15, wherein the parameter of the flow sensitive gradient block further includes a component on a slice selecting axis, a component on a phase encoding axis, and a component on a readout coordinate axis, further comprising:
    determining a final duration Ts' associated with the slice selecting axis, a final duration Tp' associated with the phase encoding axis, and a final duration Tr' associated with the readout coordinate axis, respectively; and
    determining a shared duration T' for the slice selecting axis, the phase encoding axis, and the readout coordinate axis based on the final durations.

17. The method of claim 11, wherein the imaging sequence further comprises a second echo, and the method further comprising:
    determining an imaging gradient parameter for the second echo;
    determining a second time origin for gradient moment calculation based on the imaging gradient parameter for the second echo;
    obtaining at least a target zeroth-order gradient moment and a target first-order gradient moment corresponding to the second time origin;
    determining a second parameter of a second flow sensitive gradient block with respect to the target zeroth-order gradient moment and the target first-order gradient moment, the second flow sensitive gradient block including at least one flow sensitive gradient, the second parameter of the second flow sensitive gradient block including at least one duration and at least one amplitude value of the at least one flow sensitive gradient;
    modifying the second parameter of the second flow sensitive gradient block by adjusting a duration of the second flow sensitive gradient block iteratively, wherein the duration of the second flow sensitive gradient block is determined based on the at least one duration of the at least one flow sensitive gradient corresponding to the second flow sensitive gradient block; and
    updating the imaging gradient parameter by inserting the modified second flow sensitive gradient block into the imaging gradient parameter.

18. The method of claim 17, wherein the target zeroth-order gradient moment and the target first-order gradient moment corresponding to the time origin are independent of the target zeroth-order gradient moment and the target first-order gradient moment corresponding to the second time origin.

19. The method of claim 11, further comprising:
exciting nuclear spins in a volume of a subject based on the updated imaging gradient parameter, wherein the volume comprises a flow;
acquiring magnetic resonance signals for the volume; and
generating a magnetic resonance image of the volume with the flow based on the magnetic resonance signals.

20. A non-transitory computer readable medium embodying a computer program product, the computer program product comprising instructions configured to cause a computing device to:
determine an imaging gradient parameter for one or more echoes in an imaging sequence;
determine one or more time origins for gradient moment calculation based on the gradient parameter;
obtain one or more target zeroth-order gradient moments and one or more target first-order gradient moments corresponding to the one or more time origins, respectively;
determine one or more parameters of one or more flow sensitive gradient blocks with respect to the one or more target zeroth-order gradient moments and the one or more target first-order gradient moments, wherein each of the one or more flow sensitive gradient blocks includes at least one flow sensitive gradient, the parameter of each of the one or more flow sensitive gradient blocks includes at least one duration and at least one amplitude value of the at least one flow sensitive gradient;
modify each of the one or more parameters of the one or more flow sensitive gradient blocks by adjusting a corresponding duration of the flow sensitive gradient block iteratively, wherein the duration of the flow sensitive gradient block is determined based on the at least one duration of the at least one flow sensitive gradient corresponding to the flow sensitive gradient block; and
update the image gradient parameter according to the modified one or more parameters of the one or more flow sensitive gradient blocks.

* * * * *